(12) United States Patent
Guo et al.

(10) Patent No.: US 11,251,791 B2
(45) Date of Patent: Feb. 15, 2022

(54) MICROFLUID DETECTION DEVICE, SYSTEM AND METHOD, PROCESSING DEVICE AND STORAGE MEDIUM

(71) Applicant: BOE Technology Group Co., Ltd., Beijing (CN)

(72) Inventors: Yuzhen Guo, Beijing (CN); Haisheng Wang, Beijing (CN); Yingming Liu, Beijing (CN); Xiaoliang Ding, Beijing (CN); Yanling Han, Beijing (CN); Xueyou Cao, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 287 days.

(21) Appl. No.: 16/455,821

(22) Filed: Jun. 28, 2019

(65) Prior Publication Data
US 2020/0007123 A1 Jan. 2, 2020

(30) Foreign Application Priority Data

Jul. 2, 2018 (CN) .......................... 201810708951.2

(51) Int. Cl.
*H03K 17/687* (2006.01)
*G01N 21/03* (2006.01)
*G01N 33/50* (2006.01)

(52) U.S. Cl.
CPC ......... *H03K 17/6871* (2013.01); *G01N 21/03* (2013.01); *G01N 33/50* (2013.01); *G01N 2021/0346* (2013.01)

(58) Field of Classification Search
CPC ....... B01L 2300/022; B01L 2300/0645; B01L 2300/0663; B01L 2300/0816;
(Continued)

(56) References Cited

U.S. PATENT DOCUMENTS

2003/0164295 A1* 9/2003 Sterling ............ B01L 3/502792
204/450
2014/0054174 A1 2/2014 Wang
(Continued)

FOREIGN PATENT DOCUMENTS

CN 102671724 A 9/2012
CN 104903003 A 9/2015
(Continued)

OTHER PUBLICATIONS

See attached translation of CN-107527595-A (Year: 2017).*
First office action of Chinese application No. 201810708951.2 dated May 25, 2020.

*Primary Examiner* — Jennifer Wecker
*Assistant Examiner* — Jonathan Bortoli
(74) *Attorney, Agent, or Firm* — Fay Sharpe LLP

(57) ABSTRACT

Disclosed are a microfluid detection device, system and method, a processing device and a storage medium, in the field of biochemistry. The device includes a first substrate and a second substrate facing each other, and a microfluid chamber between the first substrate and the second substrate; wherein the first substrate has a plurality of photoelectric sensors and an output circuit, each of the photoelectric sensors is configured to convert an optical signal passing through the second substrate and the microfluid chamber to an electrical signal, and the output circuit is configured to output the electrical signal obtained by the photoelectric sensor.

19 Claims, 12 Drawing Sheets

(58) Field of Classification Search
CPC ....... B01L 2300/0887; B01L 2300/161; B01L 2400/0427; B01L 3/502715; B01L 3/50273; B01L 3/502792; G01N 2021/0346; G01N 21/03; G01N 21/3577; G01N 21/359; G01N 33/50; H03K 17/6871

See application file for complete search history.

(56) References Cited

U.S. PATENT DOCUMENTS

| | | | |
|---|---|---|---|
| 2018/0043687 A1* | 2/2018 | Govyadinov | B41J 2/125 |
| 2019/0092623 A1 | 3/2019 | Ding et al. | |
| 2019/0097076 A1 | 3/2019 | Cao et al. | |
| 2020/0108387 A1 | 4/2020 | Dong et al. | |

FOREIGN PATENT DOCUMENTS

| | | | |
|---|---|---|---|
| CN | 107209107 A | 9/2017 |
| CN | 107527595 A | 12/2017 |
| CN | 107607475 A | 1/2018 |
| CN | 107649223 A | 2/2018 |
| CN | 107754962 A | 3/2018 |

\* cited by examiner

MICROFLUID DETECTION DEVICE, SYSTEM AND METHOD, PROCESSING DEVICE AND STORAGE MEDIUM

CROSS-REFERENCE TO RELATED APPLICATION

This application claims priority to Chinese Patent Application No.: 201810708951.2, filed on Jul. 2, 2018 and entitled "MICROFLUID DETECTION DEVICE AND METHOD", the entire contents of which are incorporated herein by reference.

TECHNICAL FIELD

The present disclosure relates to the field of biochemistry, and more particular to a microfluid detection device, system and method, a processing device and a storage medium.

BACKGROUND

In the scientific experiments, such as biology, chemistry and materials, microfluid detection devices are usually adopted to detect the composition of microfluid. The microfluid may be a deoxyribo nucleic acid (DNA) sample. The microfluid detection device plays an important role in aspects, such as cell diagnostic tests, medical product development or cosmetic surgery.

SUMMARY

Embodiments of the present disclosure provide a microfluid detection device, system and method, a processing device and a storage medium.

At least one embodiment of the present disclosure provides a microfluid detection device, comprising: a first substrate and a second substrate facing each other, and a microfluid chamber between the first substrate and the second substrate; wherein the first substrate has a plurality of photoelectric sensors and an output circuit connected to the plurality of photoelectric sensors, each of the photoelectric sensors is configured to convert an optical signal passing through the second substrate and the microfluid chamber to an electrical signal, and the output circuit is configured to output the electrical signal obtained by the photoelectric sensor.

Optionally, the output circuit comprises: a plurality of first switching sub-circuits in a one-to-one correspondence with the plurality of photoelectric sensors, wherein each of the first switching sub-circuits has an input terminal, an output terminal, and a first control terminal, and the input terminal of the first switching sub-circuit is connected to the corresponding photoelectric sensor; and each of the first switching sub-circuits is configured to output the electrical signal obtained by the corresponding photoelectric sensor from the output terminal of the first switching sub-circuit under the control of a control signal provided by the first control terminal.

Optionally, the first switching sub-circuit comprises: a first switching transistor, wherein a gate electrode of the first switching transistor is connected to the first control terminal, a first electrode of the first switching transistor is connected to the input terminal of the first switching sub-circuit, and a second electrode of the first switching transistor is connected to the output terminal of the first switching sub-circuit.

Optionally, the plurality of first switching sub-circuits is disposed in an array on the first substrate; first control terminals of the plurality of first switching sub-circuits disposed along a first direction are connected to a same control line, and output terminals of the plurality of first switching sub-circuits disposed along a second direction are connected to a same signal line; wherein the first direction is one of a row direction and a column direction, and the second direction is the other one of the row direction and the column direction.

Optionally, the microfluid detection device further comprises: at least one of a first hydrophobic layer and a second hydrophobic layer, wherein the first hydrophobic layer is on a side surface, close to the microfluid chamber, of the first substrate and the second hydrophobic layer is on a side surface, close to the microfluid chamber, of the second substrate.

Optionally, the microfluid detection device further comprises: a drive circuit, configured to provide an electric field acting on a target hydrophobic layer; wherein the target hydrophobic layer is configured to change in hydrophobicity under the action of the electric field, to drive microfluid to move within the microfluid chamber; and the target hydrophobic layer comprises at least one of the first hydrophobic layer and the second hydrophobic layer.

Optionally, the drive circuit comprises: a power source terminal, configured to provide a power source signal; a plurality of drive sub-circuits, configured to provide an electric field to different regions of the target hydrophobic layer; and a plurality of second switching sub-circuits, wherein the plurality of second switching sub-circuits are in a one-to-one correspondence with the plurality of drive sub-circuits, the second switching sub-circuit has an input terminal, an output terminal, and a second control terminal, the input terminal of the second switching sub-circuit is connected to the power source terminal, the output terminal of the second switching sub-circuit is connected to the corresponding drive sub-circuit, and the second switching sub-circuit is configured to transmit the power source signal provided by the power source terminal to the corresponding drive sub-circuit under the control of a control signal provided by the second control terminal, to enable the corresponding drive sub-circuit to provide an electric field to the target hydrophobic layer.

Optionally, each of the drive sub-circuits comprises a first electrode and a second electrode, each of the second switching sub-circuits is connected to the first electrode in the corresponding drive sub-circuit respectively, and the second switching sub-circuit is on the same substrate as the first electrode; and the first electrode and the second electrode in each of the drive sub-circuits are disposed in any one of the following manners: the first electrode and the second electrode are spaced apart from each other in an insulating manner at a side, close to the microfluid chamber, of the first substrate; the first electrode and the second electrode are spaced apart from each other in an insulating manner at a side, close to the microfluid chamber, of the second substrate; the first electrode is at a side, close to the microfluid chamber, of the first substrate, and the second electrode is at a side, close to the microfluid chamber, of the second substrate; and the first electrode is at a side, close to the microfluid chamber, of the second substrate, and the second electrode is at a side, close to the microfluid chamber, of the first substrate.

Optionally, the second electrodes in the plurality of drive sub-circuits are of an integral structure; and an orthographic projection of the first electrode on the substrate which the second electrode is on and the integral structure meet any one of the following relationships: the integral structure is grid-shaped, and the orthographic projection of the first electrode on the substrate which the second electrode is on is within a grid of the grid-shaped integral structure; and the integral structure is block-shaped, and the orthographic projection of the first electrode on the substrate which the second electrode is on is within the block-shaped integral structure.

Optionally, the first electrodes and the second electrodes in the plurality of drive sub-circuits are disposed in an array; and the substrate which the second electrodes are on has a plurality of regions in an array, and each of the regions has one of the first electrodes and one of the second electrodes which are spaced apart.

Optionally, each of the second switching sub-circuits comprises: a second switching transistor; wherein a gate electrode of the second switching transistor is connected to the second control terminal, a first electrode of the second switching transistor is connected to the input terminal of the second switching sub-circuit, and a second electrode of the second switching transistor is connected to the output terminal of the second switching sub-circuit.

Optionally, the target hydrophobic layer is made of polytetrafluoroethylene.

At least one embodiment of the present disclosure provides a microfluid detection system, comprising: a microfluid detection device and a processing device, wherein the microfluid detection device comprises: a first substrate and a second substrate facing each other, and a microfluid chamber between the first substrate and the second substrate; the first substrate has a plurality of photoelectric sensors and an output circuit connected to the plurality of photoelectric sensors, each of the photoelectric sensors is configured to convert an optical signal passing through the second substrate and the microfluid chamber to an electrical signal, and the output circuit is configured to output the electrical signal obtained by the photoelectric sensor; and the processing device is connected to the output circuit, and the processing device is configured to receive the electrical signal output by the output circuit and to determine composition of microfluid based on the received electrical signal.

At least one embodiment of the present disclosure provides a microfluid detection method, applied to the microfluid detection device described above. The method comprises: receiving the electrical signal output by the output circuit; and determining composition of microfluid based on the received electrical signal.

Optionally, determining the composition of microfluid based on the received electrical signal comprises: determining, according to magnitude of the electrical signal, the composition of the microfluid from a prestored first corresponding relationship, wherein the first corresponding relationship is configured to record a corresponding relationship between the magnitude of the electrical signal and the composition of the microfluid, and the magnitude of the electrical signal is voltage magnitude of the electrical signal or the current magnitude of the electrical signal.

Optionally, the output circuit comprises: a plurality of first switching sub-circuits in a one-to-one correspondence with the plurality of photoelectric sensors, wherein each of the first switching sub-circuits has an input terminal, an output terminal, and a first control terminal, and the input terminal of the first switching sub-circuit is connected to the corresponding photoelectric sensor; and the method further comprises: providing a control signal to the first control terminal, to enable the first switching sub-circuit to output the electrical signal obtained by the corresponding photoelectric sensor from the output terminal of the first switching sub-circuit under the control of the control signal provided by the first control terminal.

Optionally, the microfluid detection device further comprises at least one of a first hydrophobic layer and a second hydrophobic layer, and a drive circuit, wherein the first hydrophobic layer is on a side surface, close to the microfluid chamber, of the first substrate and the second hydrophobic layer is on a side surface, close to the microfluid chamber, of the second substrate; the method further comprises: controlling the drive circuit to generate an electric field acting on a target hydrophobic layer, wherein the target hydrophobic layer is configured to change in hydrophobicity under the action of the electric field, to drive the microfluid to move within the microfluid chamber; wherein the target hydrophobic layer comprises at least one of the first hydrophobic layer and the second hydrophobic layer.

Optionally, the method further comprises: determining, based on the received electrical signal, at least one piece of the following information: a position, height, and a volume of the microfluid.

At least one embodiment of the present disclosure provides a processing device, comprising: a processor; and a memory configured to store instructions executable by the processor; wherein the processor is configured to implement the methods described above.

At least one embodiment of the present disclosure provides a computer readable storage medium, capable of implementing the methods described above when instructions in the computer readable storage medium are executed by a processor

BRIEF DESCRIPTION OF THE DRAWINGS

FIG. 11 is a distribution diagram of magnitude of an optical signal received by a photoelectric sensor according to an embodiment of the present disclosure; and.

DETAILED DESCRIPTION

Figure 1:
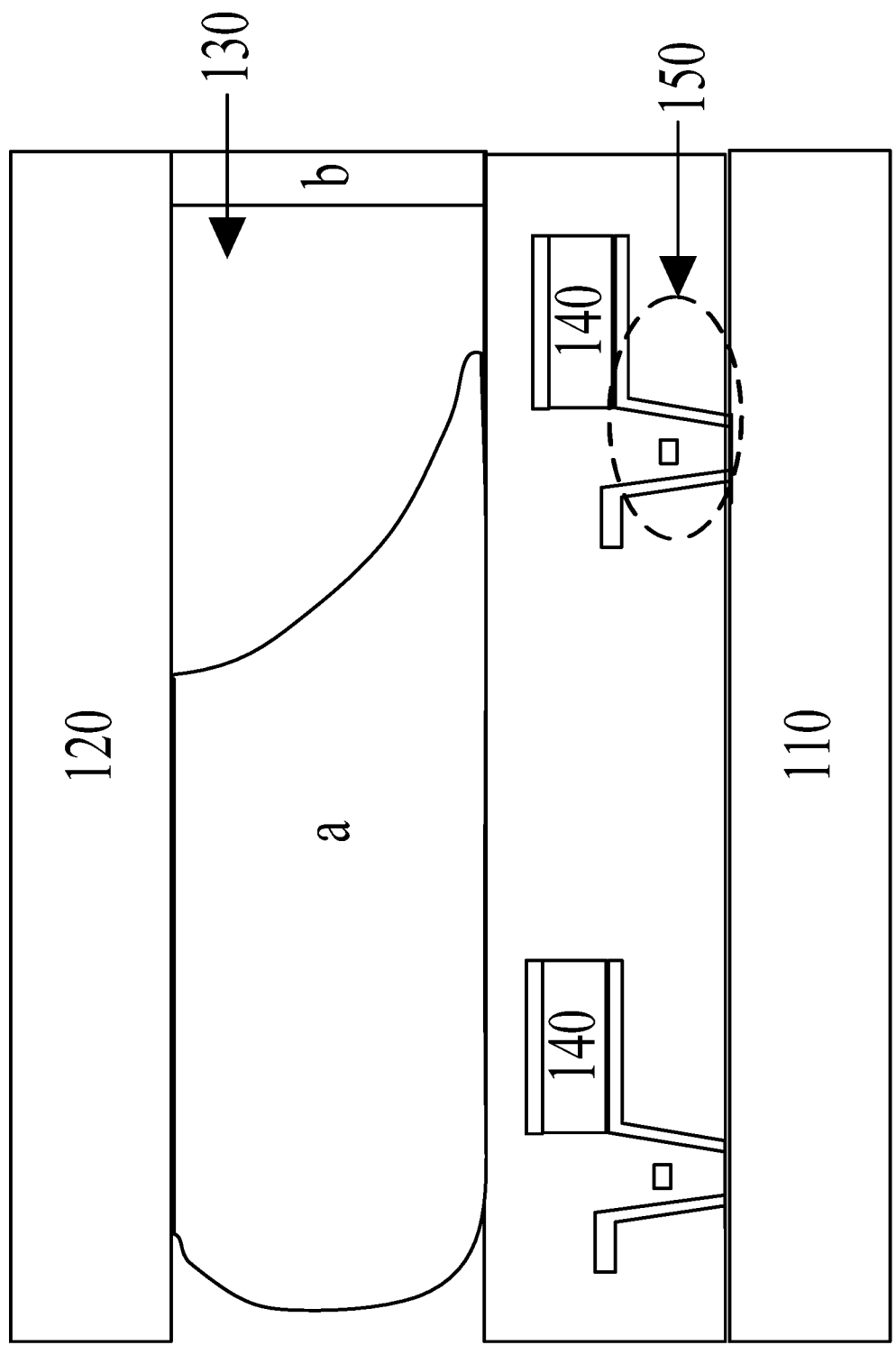
FIG. 1 is a schematic structural diagram of a microfluid detection device according to an embodiment of the present disclosure.

Embodiments of the present disclosure will be described in further detail with reference to the accompanying drawings, to present the principles and advantages of the present disclosure more clearly.

In the related art, the microfluid detection device generally includes a containing cavity for containing microfluid, a plurality of capacitors, and a detection device. Here, the plurality of capacitors is disposed on one side of the containing cavity and is connected to the detection device. In the process of irradiating the microfluid with a light source, the detection device can detect the capacitance values corresponding to the plurality of capacitors, and can determine the composition of the microfluid according to the capacitance values.

However, due to change of composition of the microfluid, the capacitance values of the capacitors change slightly. Therefore, the accuracy of detecting the composition of the microfluid according to the capacitance values is relatively low.

The transistors adopted in all embodiments of the present disclosure may be thin film transistors or field effect transistors or other devices having the same characteristics. The transistors adopted in the embodiments of the present disclosure are mainly switching transistors according to the functions in the circuit. Since the source electrode and the drain electrode of the switching transistor adopted here are symmetrical, the source electrode and the drain electrode are interchangeable. In the embodiments of the present disclosure, the source electrode is referred to as a first electrode and the drain electrode is referred to as a second electrode. According to the form in the drawings, the middle end of the transistor is specified as the gate electrode, the signal input terminal is specified as the source electrode, and the signal output terminal is specified as the drain electrode. In addition, the switching transistors adopted in the embodiments of the present disclosure may include any one of a P-type switching transistor and an N-type switching transistor. Here, the P-type switching transistor is turned on when the gate electrode is at a low level, and is turned off when the gate electrode is at a high level. The N-type switching transistor is turned on when the gate electrode is at a high level and turned off when the gate electrode is at a low level. In addition, the plurality of signals in the varied embodiments of the present disclosure corresponds to a first potential and a second potential respectively. The first potential and the second potential only represent two state quantities of the potential of the signal, and do not represent that the first potential or the second potential in the whole text has a specific value.

An embodiment of the present disclosure provides a microfluid detection device, which can solve the problem of relatively low accuracy in detection composition of liquid in the related art. As shown in FIG. 1, the device may include: a first substrate 110 and a second substrate 120 facing each other and a microfluid chamber 130 disposed between the two substrates (i.e., the first substrate 110 and the second substrate 120).

A plurality of photoelectric sensors 140 and an output circuit connected to the plurality of photoelectric sensors 140 are disposed at a side, close to the microfluid chamber 130, of the first substrate 110. Each photoelectric sensor 140 is configured to convert an optical signal passing through the second substrate 120 and the microfluid chamber 130 into an electrical signal, and the output circuit is configured to output the electrical signal obtained by the photoelectric sensor 140.

Exemplarily, the photoelectric sensor 140 may be a Positive Intrinsic Negative (PIN) photoelectric sensor, which may also be referred to as a photosensitive sensor.

The microfluid chamber 130 is configured to contain microfluid a, which may be liquid, such as amino acid, protein, or salt. The microfluid chamber 130 may be formed by the first substrate 110, the second substrate 120, and a spacer b disposed between the first substrate 110 and the second substrate 120. An opening may further be disposed at end of the microfluid chamber 130, to facilitate injection of the microfluid. In some embodiments, the microfluid chamber 130 may include one or more microfluid channels. The opening may be at the end part of the microfluid channel or at the intersection of the connected microfluid channels.

Exemplarily, the photoelectric sensors 140 may be evenly distributed within the orthographic projection range of the microfluid chamber 130 on the first substrate 110.

Exemplarily, the output circuit may be connected to a processing device, and the processing device may determine the composition of the microfluid based on the electrical signal output by the output circuit. The processing device may be an independent device, such as a computer device which is electrically connected to the microfluid detection device shown in FIG. 1, or may be integrated with the above-described microfluid detection device. For example, the processing device may be a processing chip integrated in the microfluid detection device in FIG. 1, which is not limited in the present embodiments of the present disclosure.

Exemplarily, in the embodiment of FIG. 1, the output circuit includes a plurality of first switching sub-circuits 150 in a one-to-one correspondence with the plurality of photoelectric sensors 140. Each of the first switching sub-circuits 150 is has an input terminal, an output terminal and a first control terminal. The input terminal is connected to the corresponding photoelectric sensor 140. Each of the first switching sub-circuits 150 is configured to output the electrical signal obtained by the corresponding photoelectric sensor 140 from the output terminal under the control of a control signal provided by the first control terminal.

Correspondingly, in the embodiment of the present disclosure, the microfluid a may be firstly injected into the microfluid chamber 130, and then the microfluid detection device containing the microfluid a is irradiated with different light sources, which may be ambient light, or infrared light, etc. Under the control of the control signal provided by the first control terminal, the plurality of first switching sub-circuits 150 is selectively turned on, to output the electrical signal obtained by the corresponding photoelectric sensor 140 from the output terminal. Subsequently, based on the outputted electrical signal, the microfluid is detected to determine the composition of the microfluid.

Since light needs to pass through the second substrate 120, the second substrate 120 may be transparent to reduce the influence on the light. Exemplarily, the second substrate 120 may be a glass substrate, a plastic substrate or the like.

Optionally, the output circuit may further include at least one control line. The first control terminal is connected to the control line, and the control line is configured to input a control signal to the connected first control terminal.

Optionally, the output circuit may further include at least one data line. The output terminal is connected to the data line, and the data line is configured to output the electrical signal output by the connected output terminal to an external detection device.

Alternatively, in some embodiments, the output circuit may also only include a plurality of data lines in one-to-one correspondence with the plurality of photoelectric sensors 140, and do not include the first switching sub-circuits. The data lines are configured to output the detection signals obtained by the corresponding photoelectric sensors 140, respectively.

Exemplarily, the composition of the microfluid may be determined from a prestored first corresponding relationship according to the magnitude of the electrical signal. The first corresponding relationship records the corresponding relationship between the magnitude of the electrical signal and the composition of the microfluid, and can be obtained by experiments. Moreover, the magnitude of the electrical signal may refer to the voltage magnitude of the electrical signal, and may also refer to the current magnitude of the electrical signal, which is not limited in the embodiments of the present disclosure.

In summary, the microfluid detection device provided by the embodiment of the present disclosure includes a first substrate and a second substrate facing each other, and a microfluid chamber disposed between the two substrates. A plurality of photoelectric sensors and a plurality of first switching sub-circuits in a one-to-one correspondence with the plurality of photoelectric sensors are disposed on one side, close to the microfluid chamber, of the first substrate, and each of the first switching sub-circuits is connected to the corresponding photoelectric sensor, the processing device and the first control terminal respectively. Since each photoelectric sensor can convert an optical signal passing through the microfluid into an electrical signal and transmit the electrical signal to the processing device though the corresponding first switching sub-circuit. The processing device determines the composition of the microfluid according to the magnitude of the received electrical signal. Compared with the related art, the photoelectric sensors are more sensitive in detection of the change in composition of the microfluid, thereby improving the accuracy of detection of composition of the microfluid. The embodiment of the present disclosure realizes integrated detection of the microfluid by integrating the photoelectric sensors, the first switching sub-circuits, and the microfluid chamber on the substrates.

It should be noted that, in the embodiment shown in FIG. 1, the photoelectric sensors 140 and the output circuit are both on one side, close to the microfluid chamber 130, of the first substrate 110, so that the first substrate 110 can play a role of protection. In other embodiments, the photoelectric sensors 140 and the output circuit may also be on one side, away from the microfluid chamber 130, of the first substrate 110.

Figure 2:
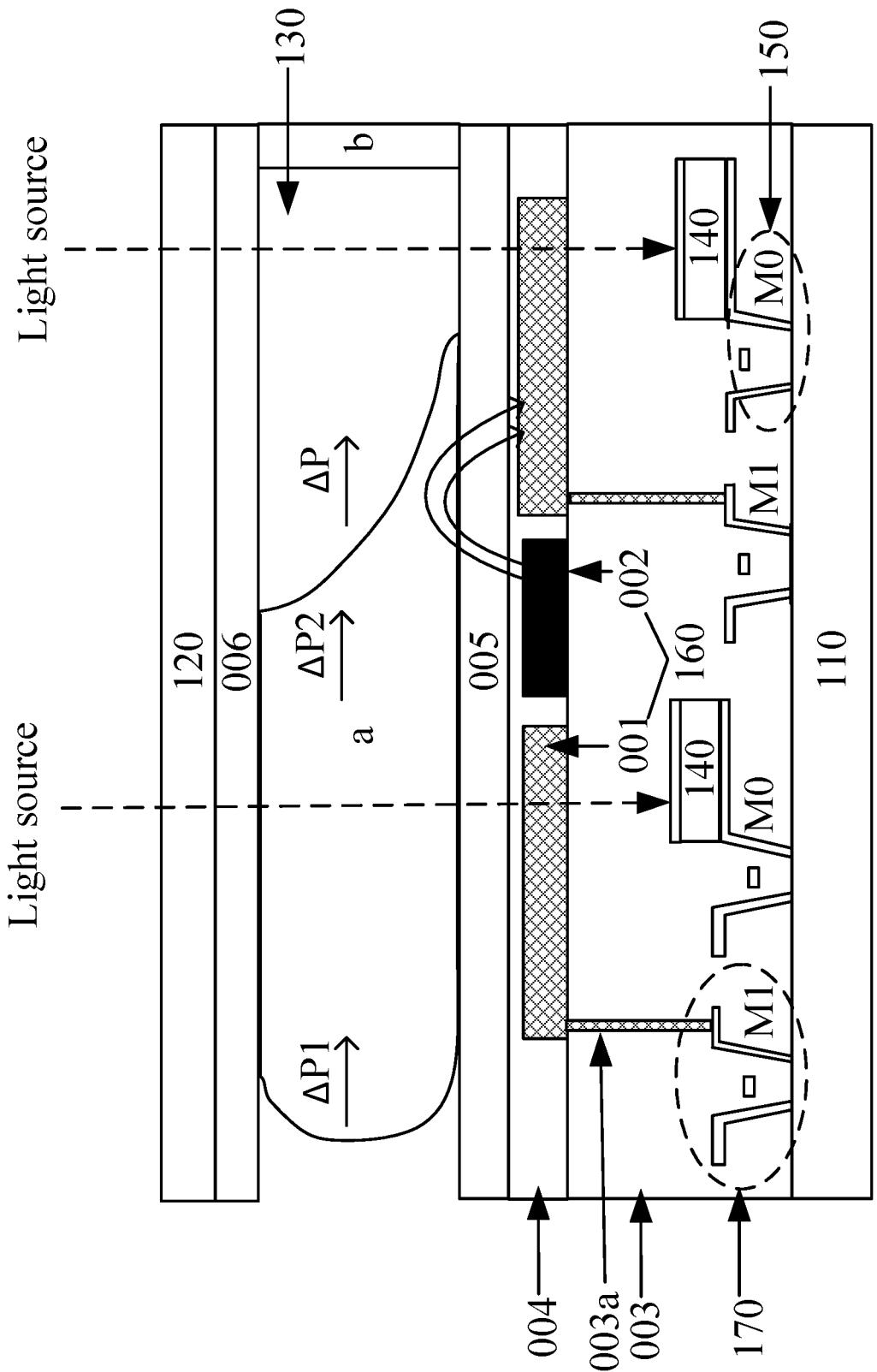
FIG. 2 is a schematic structural diagram of another microfluid detection device according to an embodiment of the present disclosure.

FIG. 2 is a schematic structural diagram of another microfluid detection device according to the embodiment of the present disclosure. Optionally, as shown in FIG. 2, in addition to the structure shown in FIG. 1, the device may further include: a first hydrophobic layer 005 disposed on one side, close to the microfluid chamber 130, of the first substrate 110, and a second hydrophobic layer 006 disposed on one side, close to the microfluid chamber 130, of the second substrate 120.

In the embodiment of the present disclosure, the viscosity coefficient of the microfluid can be reduced by disposing the first hydrophobic layer and the second hydrophobic layer. Exemplarily, the first hydrophobic layer and the second hydrophobic layer may be made from a low surface energy material, such as a fluorine material.

Optionally, in the microfluid detection device in other embodiments, only the first hydrophobic layer 005 or only the second hydrophobic layer 006 may be disposed.

Exemplarily, the hydrophobicity of at least one of the first hydrophobic layer and the second hydrophobic layer can be changed under the action of an electric field, and such hydrophobic layer may be referred to as an adjustable hydrophobic layer. That is, when the electric field passes through partial regions of the adjustable hydrophobic layer, the hydrophobicity of the adjustable hydrophobic layer in the regions where the electric field acts changes. Exemplarily, the adjustable hydrophobic layer may be made from a polytetrafluoroethylene or siloxane material, etc.

Accordingly, the device may further include a drive circuit configured to provide an electric field acting on a target hydrophobic layer. The target hydrophobic layer is configured to change in hydrophobicity under the action of the electric field, to drive the microfluid a to move within the fluid cavity 130. That is, the target hydrophobic layer is the above-described adjustable hydrophobic layer. In the embodiment of the present disclosure, the target hydrophobic layer is at least one of the first hydrophobic layer and the second hydrophobic layer.

Exemplarily, as shown in FIG. 2, the drive circuit may include: a power source terminal, a plurality of drive sub-circuits 160, and a plurality of second switching sub-circuits 170 in a one-to-one correspondence with the plurality of drive sub-circuits 160. The plurality of drive sub-circuits 160 and the plurality of second switching sub-circuits 170 may be both on the side, close to the microfluid chamber 130, of the substrate (which may be the first substrate 110 or the second substrate 120).

Here, the power source terminal is configured to provide a power source signal. The plurality of drive sub-circuits 160 is configured to provide the electric field to different regions of the target hydrophobic layer. The second switching sub-circuit 170 has an input terminal, an output terminal and a second control terminal. The input terminal of the second switching sub-circuit 170 is connected to the power source terminal, and the output terminal of the second switching sub-circuit 170 is connected to the corresponding drive sub-circuit 160. The second switching sub-circuit 170 is configured to transmit the power source signal provided by the power source terminal to the corresponding drive sub-circuit 160 under the control of the control signal provided by the second control terminal, to enable the corresponding drive sub-circuit 160 to provide an electric field to the target hydrophobic layer. Therefore, the microfluid a is driven to move within the microfluid chamber 130 to move to a designated position within the microfluid chamber 130.

Exemplarily, in the embodiment of the present disclosure, the microfluid chamber may contain different types of microfluid. By driving different types of microfluid to the same position, different types of microfluid can react with each another, and thereby the composition of the microfluid after the reaction can be detected by the microfluid detection device.

Exemplarily, the level of the power source signal provided by the power source terminal may be a high level.

In an optional implementation, as shown in FIG. 2, the plurality of drive sub-circuits 160 and the plurality of second switching sub-circuits 170 may be both at one side, close to the microfluid chamber 130, of the first substrate 110.

In another optional implementation, the plurality of drive sub-circuits 160 and the plurality of second switching sub-circuits 170 may also be both on one side, close to the microfluid chamber 130, of the second substrate 120.

In yet another optional implementation, a portion of each of the drive sub-circuits 160 is on one side, close to the microfluid chamber 130, of the first substrate 110, and other portion of each of the drive sub-circuits 160 and the plurality of second switching sub-circuit 170 are on one side, close to the microfluid chamber 130, of the second substrate 120.

Optionally, as shown in FIG. 2, each of the drive sub-circuits 160 may include a first electrode 001 and a second electrode 002. Each of the second switching sub-circuits 170 may be connected to the first electrode 001 in the corresponding drive sub-circuit 160 respectively, and the second switching sub-circuit 170 and the first electrode 001 are on the same substrate. For example, as shown in FIG. 2, a first insulating layer 003 may be disposed between the second switching sub-circuit 170 and the first electrode 001. Via holes 003a are disposed in the first insulating layer 003, and the second switching sub-circuit 170 may be connected to the corresponding first electrode 001 through the via hole 003a.

In the embodiment of the present disclosure, the first electrode 001 in each of the drive sub-circuits 160 may be referred to as a drive electrode, and the second electrode 002 in each of the drive sub-circuits 160 may be referred to as a common electrode (Vcom electrode). The second electrode 002 in each of the drive sub-circuits 160 may be connected to a common power source terminal VSS or may be grounded, that is, the potential provided by the signal terminal connected to the second electrode may be a constant potential.

In an optional implementation, the first electrode 001 and the second electrode 002 in each of the drive sub-circuits 160 may be spaced apart from each other on the first substrate 110 in an insulating manner. For example, as shown in FIG. 2, the first electrode 001 and the second electrode 002 in each of the drive sub-circuits 160 may be spaced apart from each other on one side, close to the microfluid chamber 130, of the first substrate 110, and a second insulating layer 004 is disposed between the first electrode 001 and the second electrode 002. As shown in FIG. 2, the whole second insulating layer 004 may cover the first substrate 110. Correspondingly, the plurality of second switching sub-circuits 170 may also be disposed on the first substrate 110.

Figure 3:
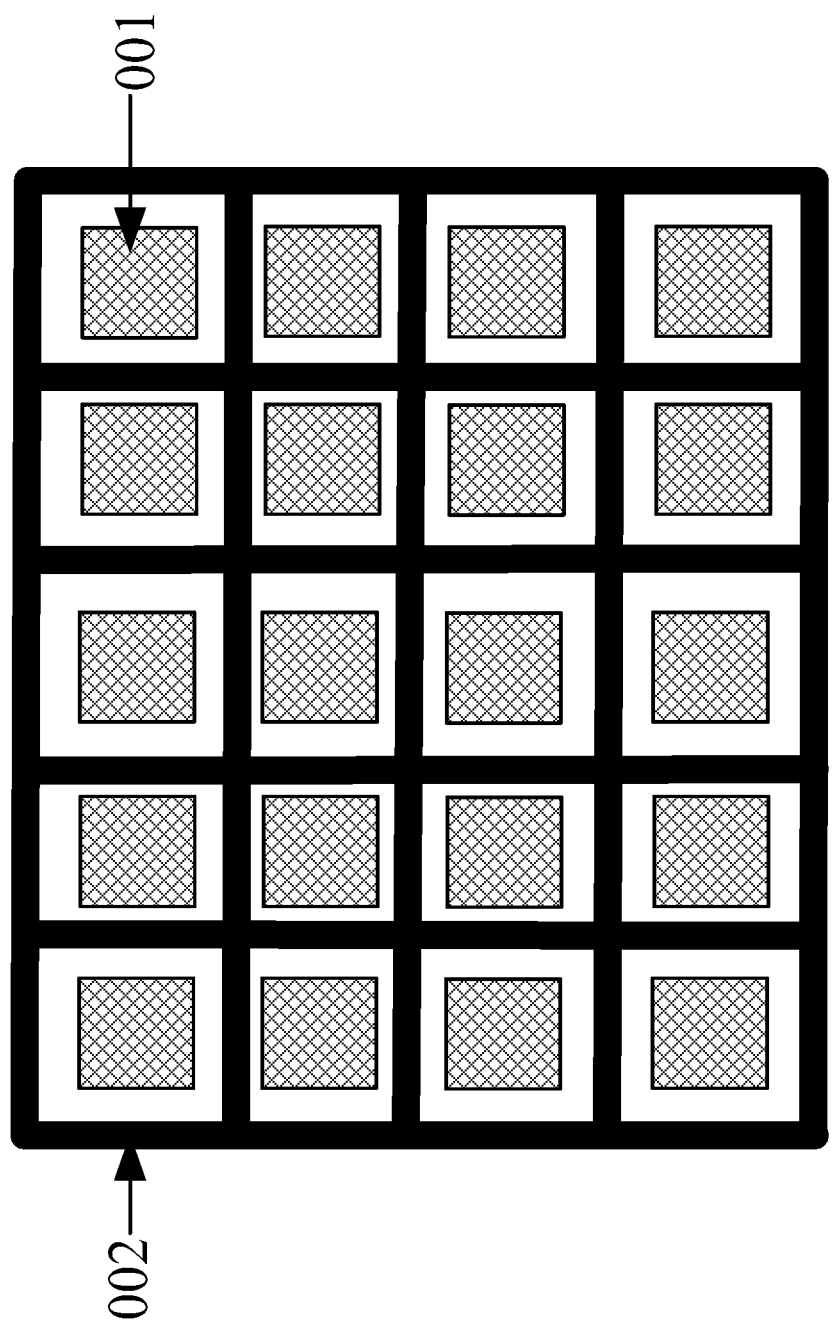
FIG. 3 is a top view of a first electrode and a second electrode according to an embodiment of the present disclosure.

FIG. 3 is a top view of a first electrode and a second electrode according to the embodiment of the present disclosure. As shown in FIG. 3, the second electrodes 002 in the plurality of drive sub-circuits 160 may be an integral structure, and the integral structure may be grid-shaped. The first electrode 001 in each of the drive sub-circuits 160 may be disposed in one grid of the integral structure.

Figure 4:
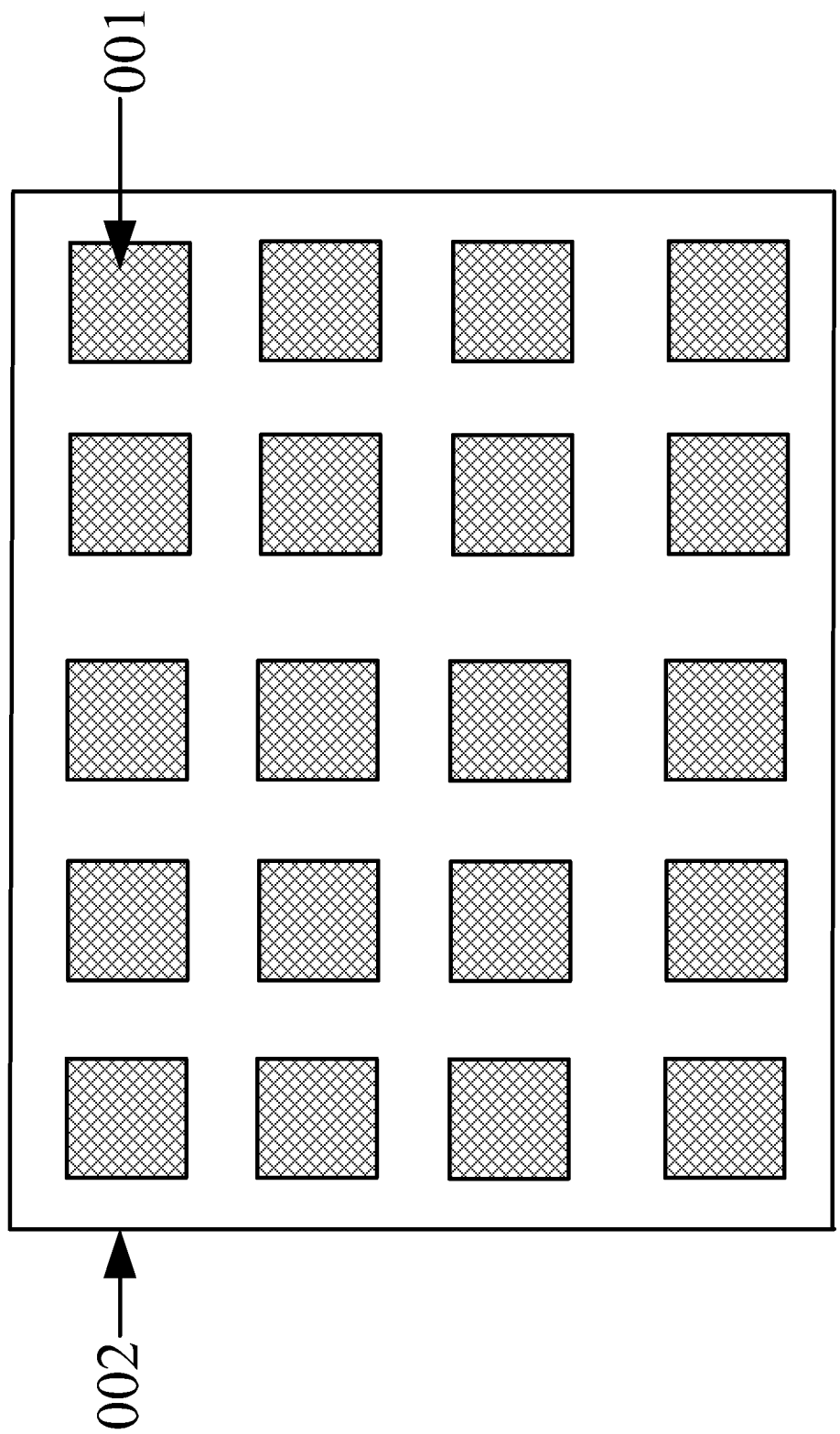
FIG. 4 is another top view of a first electrode and a second electrode according to an embodiment of the present disclosure.

FIG. 4 is another top view of the first electrode and the second electrode according to the embodiment of the present disclosure. As shown in FIG. 4, the second electrodes 002 in the plurality of drive sub-circuits 160 may be an integral structure, and the integral structure may be block-shaped. The orthographic projection of the first electrode on the substrate which the second electrode is on is within the block-shaped integral structure.

Figure 5:
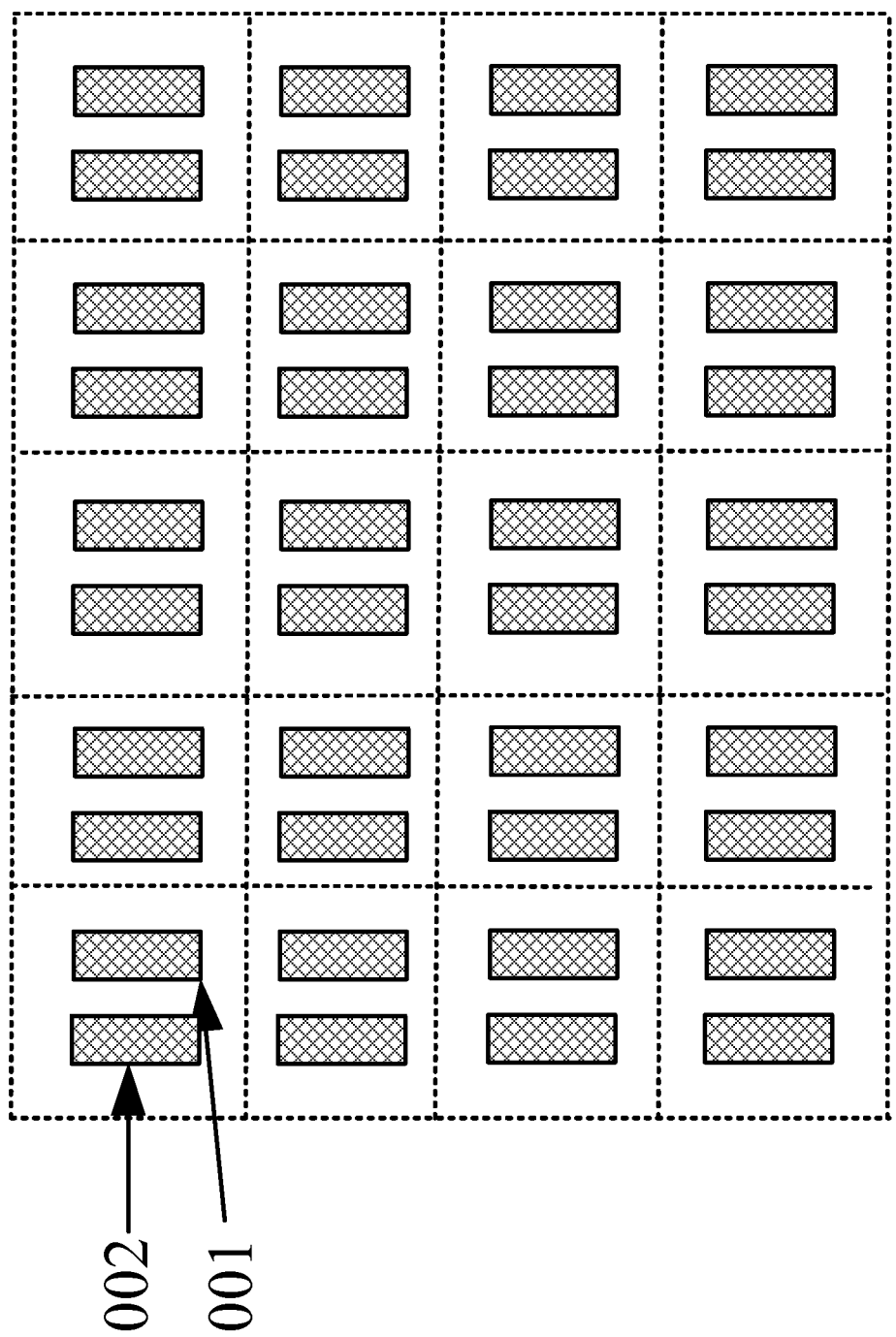
FIG. 5 is yet another top view of a first electrode and a second electrode according to an embodiment of the present disclosure.

FIG. 5 is yet another top view of the first electrode and the second electrode according to the embodiment of the present disclosure. As shown in FIG. 5, the plurality of first electrodes 001 and the plurality of second electrodes 002 may be respectively distributed in an array on the first substrate 110, and the first electrodes 001 and the second electrodes 002 are disposed in pairs. That is, the first substrate 110 has a plurality of regions in an array (as indicated by dashed boxes in FIG. 5), and each of the regions has one first electrode 001 and one second electrode 002.

In another optional implementation, the first electrode 001 and the second electrode 002 in each of the drive sub-circuits 160 may be spaced apart from each other on the second substrate 120 in an insulating manner. For example, the first electrode 001 and the second electrode 002 in each of the drive sub-circuits 160 may be spaced from each other on one side, 120 close to the microfluid chamber 130, of the second substrate 120, and a second insulating layer 004 is disposed between the first electrode 001 and the second electrode 002. Correspondingly, the plurality of second switching sub-circuits 170 may also be disposed on the second substrate 120.

In this implementation, when the microfluid detection device is viewed from the top, the first electrode 001 and the second electrode 002 may be distributed in the manner as shown in FIG. 3 or FIG. 4 or FIG. 5.

In yet another optional implementation, in each of the drive sub-circuits 160, the first electrode 001 is on the first substrate 110, and the second electrode 002 is on the second substrate 120. Alternatively, in each of the drive sub-circuits 160, the first electrode 001 is on the second substrate 120, and the second electrode 002 is on the first substrate 110. For example, one electrode (the first electrode 001 or second electrode 002) in each of the drive sub-circuits 160 may be disposed on one side, close to the microfluid chamber 130, of the first substrate 110, and the other electrode (the second electrode 002 or the first electrode 001) may be disposed on one side, close to the microfluid chamber 130, of the second substrate 120.

Figure 6:
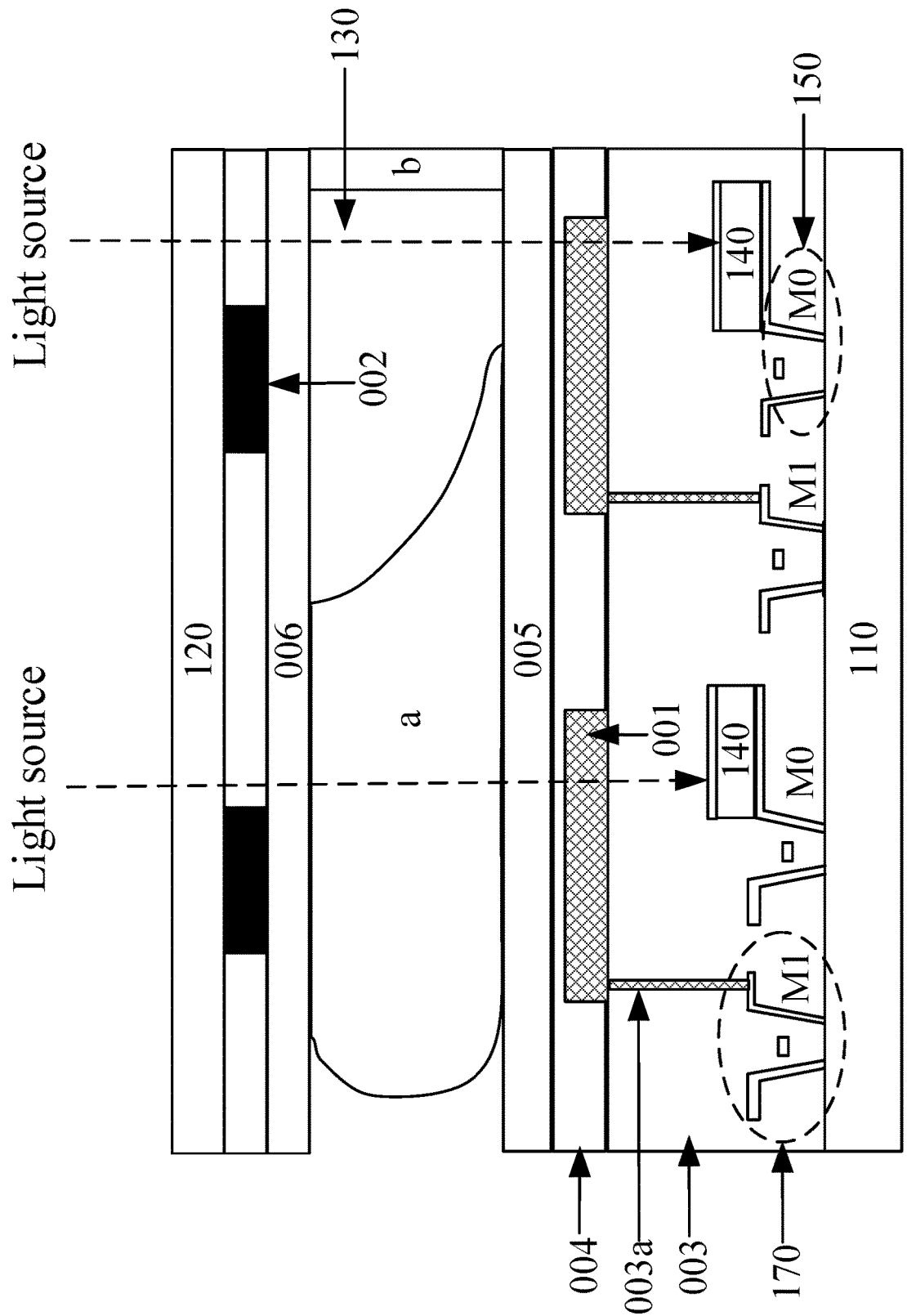
FIG. 6 is a schematic structural diagram of yet another microfluid detection device according to an embodiment of the present disclosure.

Exemplarily, as shown in FIG. 6, in each of the drive sub-circuits 160, the first electrode 001 may be disposed on one side, close to the microfluid chamber 130, of the first substrate 110, and the second electrode 002 may be disposed on one side, close to the microfluid chamber 130, of the second substrate 120.

In a possible implementation, when the microfluid detection device shown in FIG. 6 is viewed from the top, the distribution manner of the first electrodes 001 and the second electrodes 002 may be as shown in FIG. 3 or FIG. 4. That is, the second electrodes in the plurality of drive sub-circuits are of an integral structure, the integral structure is grid-shaped, and the orthographic projection of the first electrode on the substrate which the second electrode is on is within a grid of the grid-shaped integral structure. Alternatively, the integral structure is block-shaped, and the orthographic projection of the first electrode on the substrate which the second electrode is on is within the block-shaped integral structure.

In another optional implementation, when the microfluid detection device shown in FIG. 6 is viewed from the top, and the distribution manner of the first electrodes 001 and the second electrodes 002 may be as shown in FIG. 5. That is, the first electrodes and the second electrodes in the plurality of drive sub-circuits are distributed in an array. The substrate which the second electrodes are on has a plurality of regions distributed in an array, and each region has one first electrode and one second electrode which are spaced apart from each other. The orthographic projection of the first electrode 001 on the substrate which the second electrode 002 is on is spaced apart from the second electrode 002. In this implementation, the first electrode 001 and the second electrode 002 in each region can provide tilted electric field.

In another possible implementation, the orthographic projection of the first electrode 001 on the substrate which the second electrode 002 is on may coincide with the second electrode. In this implementation, the first electrode 001 and the second electrode 002 in each region can provide a vertical electric field.

It should be noted that, in order not to affect the irradiation of light onto the photoelectric sensor, both the first electrode 001 and the second electrode 002 may be transparent.

Optionally, as shown in FIG. 2, each of the first switching sub-circuits 150 may include a first switching transistor M0. A gate electrode of the first switching transistor M0 is connected to the first control terminal. A first electrode of the first switching transistor M0 is connected to the corresponding photoelectric sensor 140 (i.e., connected to the input terminal of the first switching sub-circuit 150), and a second electrode of the first switching transistor M0 is connected to the output terminal of the first switching sub-circuit 150, to facilitate connection with the detection device.

Each first switching transistor M0 may be turned on when the first control signal provided by the first control terminal is at an active level, to receive the electrical signal transmitted by the photoelectric sensor 140 via the first electrode and transmit the received electrical signal to the processing device via the second electrode. When the first switching transistor M0 is an N-type transistor, the active level may be a high level. When the first switching transistor M0 is a P-type transistor, the active level may be a low level.

Optionally, as shown in FIG. 2, each second switching sub-circuit 170 may include a second switching transistor M1. A gate electrode of the second switching transistor M1 is connected to the second control terminal. A first electrode of the second switching transistor M1 is connected to the input terminal of the second switching sub-circuit 170, to be connected to the power source terminal. A second electrode of the second switching transistor M1 is connected to the output terminal of the second switching sub-circuit 170, to be connected to the corresponding first electrode 001.

Each second switching transistor M1 may be turned on when the second control signal provided by the second control terminal is at an active level, to receive a voltage signal transmitted by the power source terminal via the first electrode, and transmit the received voltage signal to the first electrode 001 via the second electrode. When the second switching transistor M1 is an N-type transistor, the active level may be a high level. When the second switching transistor M1 is a P-type transistor, the active level may be a low level.

Exemplarily, the first switching transistor M0 and the second switching transistor M1 are disposed in the same layer, that is, they are formed by the same patterning process or substantially located in the same plane, to reduce the size of the microfluid detection device.

Exemplarily, the first switching transistors M0 and the second switching transistors M1 may be disposed in pairs, that is, the drive sub-circuits 170 and the photoelectric sensors 140 may be disposed in pairs, and one first electrode 005 corresponds to one photoelectric sensor 140. Thus, the movement accuracy and detection accuracy of the microfluid may be the same. In other implementations, the amount of the first switching transistors M0 may also be less than the amount of the second switching transistors M1. Accordingly, one first electrode 005 may correspond to a plurality of photoelectric sensors 140.

Figure 7:
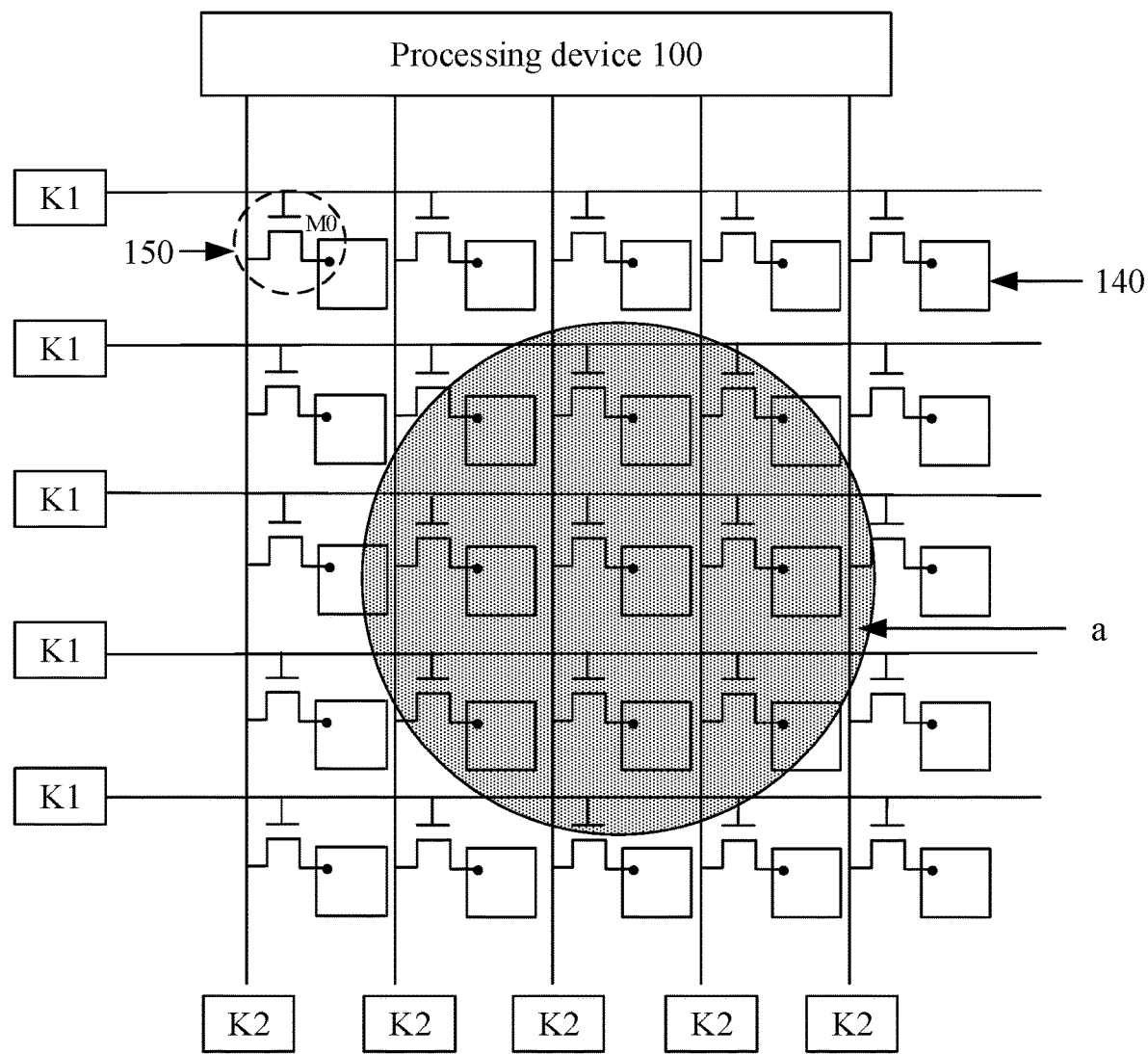
FIG. 7 is a schematic structural diagram of a first switching sub-circuit and a photoelectric sensor according to an embodiment of the present disclosure.

Optionally, FIG. 7 is a schematic structural diagram of a first switching sub-circuit and a photoelectric sensor according to the embodiment of the present disclosure. As shown in FIG. 7, the plurality of first switching sub-circuits 150 may be disposed in an array on the first substrate 110. The first switching sub-circuits 150 in the same row may be connected to the same first control terminal K1, and the first switching sub-circuits 150 in the same column are connected to the processing device 100 by the same signal line.

Correspondingly, in the detection process, the first control terminals K1 connected to the respective rows of first switching sub-circuits 150 can output first control signals at the active potential row by row, so that the respective rows of first switching sub-circuits 150 are turned on row by row and transmit the electrical signals to the processing device 100 via a signal line. The detection device 100 can determine at least one of the composition, position, height, and volume of the microfluid according to the magnitude of the received electrical signals.

In another optional implementation, the first switching sub-circuits 150 in the same column are connected to the same first control terminal K1, and the first switching sub-circuits 150 in the same row are connected to the processing device 100 by the same signal line.

Correspondingly, during the detection process, the first control terminals K1 connected to respective columns of first switching sub-circuits 150 can output first control signals at an active potential column by column, so that the respective columns of first switching sub-circuit 150 are turned on column by column and transmit electrical signals to the processing device 100 via the signal line. The processing device 100 can determine at least one of the composition, position, height, and volume of the microfluid according to the magnitude of the received electrical signals.

The driving process of the microfluid is introduced by taking the structure shown in FIG. 2 as an example. The driving process includes: each second switching sub-circuit 170 transmits the power source signal provided by the power source terminal to the corresponding first electrode 001 under the control of the control signal provided by the second control terminal, to generate an electric field between the first electrode 001 and the second electrode 002. The electric field acts on the first hydrophobic layer 005 such that the wettability, on the surface of the first hydrophobic layer 005, of the microfluid a in the region where the electric field acts (the region where the curved arrows are in FIG. 2) changes from a hydrophobic state to a hydrophilic state. Therefore, referring to FIG. 2, the intensity of pressure on the microfluid on the left side of the first electrode 001 is $\Delta P1$, the intensity of pressure on the microfluid on the right side of the first electrode 001 is $\Delta P2$, and the intensity of pressure on the entire microfluid a is $\Delta P$. Due to the intensity of pressure $\Delta P$, the microfluid a is subjected to a rightward driving force, thereby causing the microfluid a to move to the right.

In summary, the microfluid detection device provided by the embodiment of the present disclosure includes a first substrate and a second substrate facing each other, and a microfluid chamber disposed between the two substrates. A plurality of photoelectric sensors and a plurality of first switching sub-circuits in a one-to-one correspondence with the plurality of photoelectric sensors are disposed on one side, close to the microfluid chamber, of the first substrate, and each of the first switching sub-circuits is connected to the corresponding photoelectric sensor, the processing device and the first control terminal respectively. Since each photoelectric sensor can convert an optical signal passing through the microfluid into an electrical signal and output the electrical signal though the corresponding first switching sub-circuit, to determine the composition of the microfluid according to the magnitude of the received electrical signal. Compared with the related art, the photoelectric sensors are more sensitive in detection of the change in composition of the microfluid, thereby improving the accuracy of detection of composition of the microfluid.

An embodiment of the present disclosure further provides a microfluid detection system, which may include the microfluid detection device and processing device described above. The processing device is connected to the output circuit of the microfluid detection device. The processing device is configured to receive an electrical signal output by the output circuit and to determine the composition of the microfluid based on the received electrical signal.

Optionally, the processing device may determine the composition of the microfluid based on the electrical signal output by the output circuit. The processing device may be an independent device, such as a computer device which is electrically connected to the microfluid detection device. The processing device may also be integrated with the above microfluid detection device. For example, the processing device may be a processing chip integrated in the microfluid detection device.

Optionally, the system may further include a light source. The light source may be an ambient light source or an ordinary light source or a scanning light source. Here, the ordinary light source refers to a light source which emits light of a single wavelength, and the scanning light source refers to a light source capable of emitting light of changeable wavelength.

Figure 8:
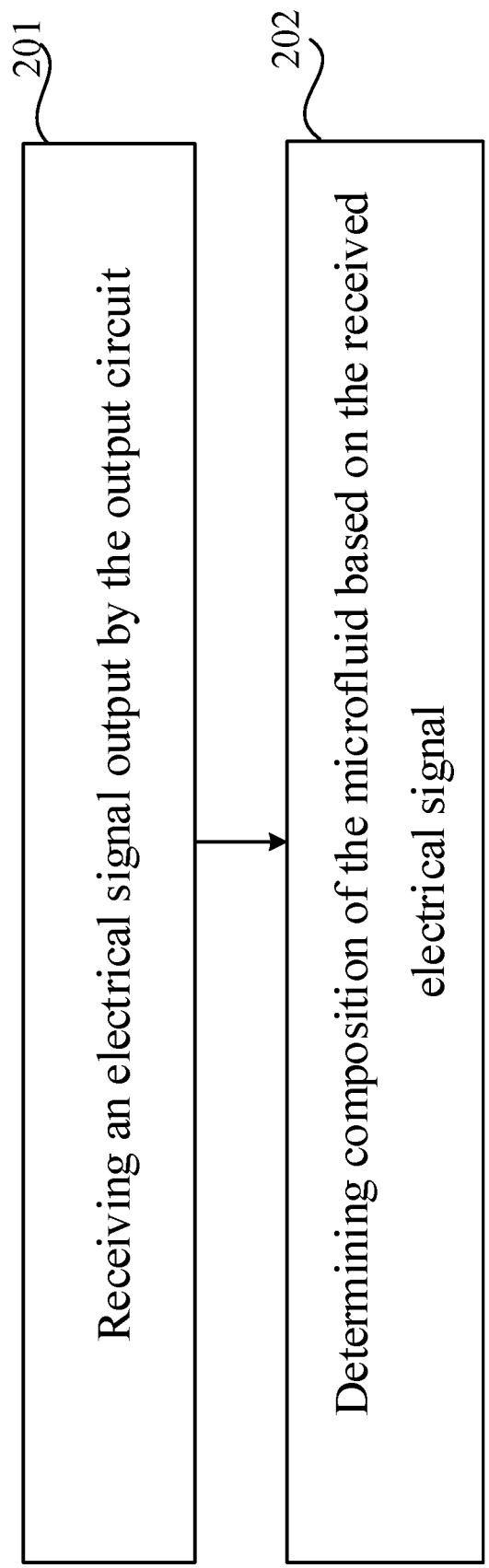
FIG. 8 is a flowchart of a microfluid detection method according to an embodiment of the present disclosure.

An embodiment of the present disclosure provides a microfluid detection method as shown in FIG. 8. The method is applied to the microfluid detection device as shown in FIG. 1 or 2. The method may be implemented by the above processing device, and the method may include the following steps.

In step 201, an electrical signal output by the output circuit is received.

In step 202, composition of the microfluid is determined based on the received electrical signal.

Exemplarily, step 202 may include: determining the composition of the microfluid from a prestored first corresponding relationship according to the magnitude of the electrical signal, wherein the first corresponding relationship records the corresponding relationship between the magnitude of the electrical signal and the composition of the microfluid.

Figure 9:
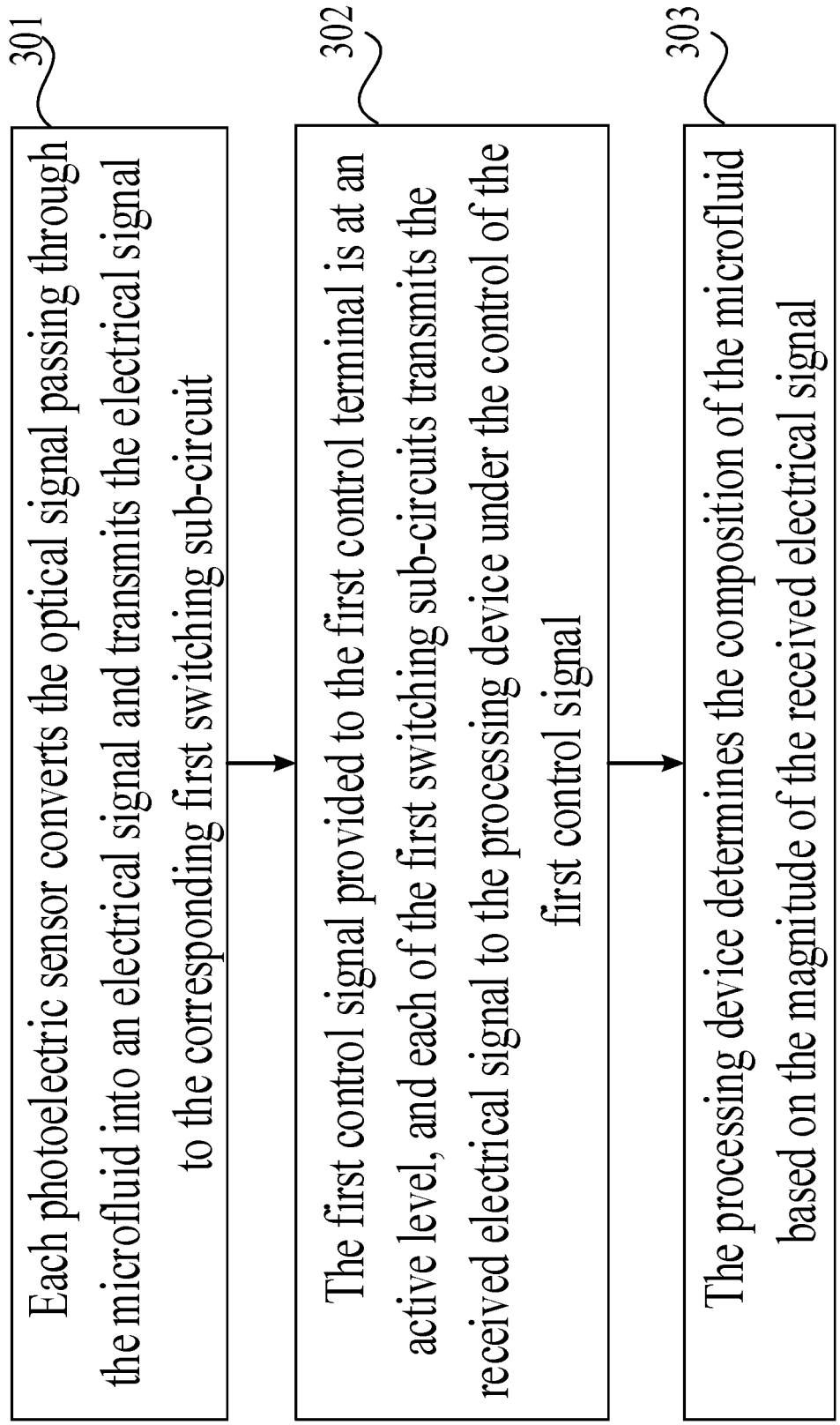
FIG. 9 is a flowchart of another microfluid detection method according to an embodiment of the present disclosure.

An embodiment of the present disclosure provides a microfluid detection method as shown in FIG. 9. The method is applied to the microfluid detection device as shown in FIG. 1 or FIG. 2. The method may include the following steps.

In step 301, each photoelectric sensor converts the optical signal passing through the microfluid into an electrical signal and transmits the electrical signal to the corresponding first switching sub-circuit.

Exemplarily, the photoelectric sensor may be a PIN photoelectric sensor. In the embodiment of the present disclosure, different light sources may be adopted to irradiate the microfluid, and light emitted by the light source passes through the microfluid a and irradiates the photoelectric sensor 140. Thus, the photoelectric sensor can convert the received optical signal into an electrical signal and transmits the electrical signal to the corresponding first switching sub-circuit. Here, the light source may be ambient light, infrared light, or the like.

In step 302, the first control signal provided to the first control terminal is at an active level, and each of the first switching sub-circuits transmits the received electrical signal to the processing device under the control of the first control signal.

Optionally, each of the first switching sub-circuits 150 may include a first switching transistor M0. Each of the first switching transistors M0 may be turned on when the first control signal provided by the first control terminal is at an active level, and receive the electrical signal transmitted by the photoelectric sensor 140 via the first electrode and transmit the received electrical signal to the processing device via the second electrode. Here, when the first switching transistor M0 is an N-type transistor, the active level may be a high level. When the first switching transistor M0 is a P-type transistor, the active level may be a low level.

In step 303, the processing device determines the composition of the microfluid based on the magnitude of the received electrical signal.

The processing device may determine the composition of the microfluid from a prestored first corresponding relationship according to the magnitude of the electrical signal, wherein the first corresponding relationship records the corresponding relationship between the magnitude of the electrical signal and the composition of the microfluid.

In summary, according to the microfluid detection method provided by the embodiment of the present disclosure, each photoelectric sensor converts the optical signal passing through the microfluid into the electrical signal, and transmits the electrical signal to the corresponding first switching sub-circuit. Each first switching sub-circuit transmits the received electrical signal to the processing device under the control of the first control signal provided by the first control terminal, so that the processing device determines the composition of the microfluid according to the magnitude of the received electrical signal. Compared with the related art, the photoelectric sensors are more sensitive in detection of change in the composition of the microfluid, thereby improving the accuracy of detection of the composition of the microfluid. With this method, real-time detection of the target microfluid can be achieved, and this method is an integrated detection method.

Figure 10:
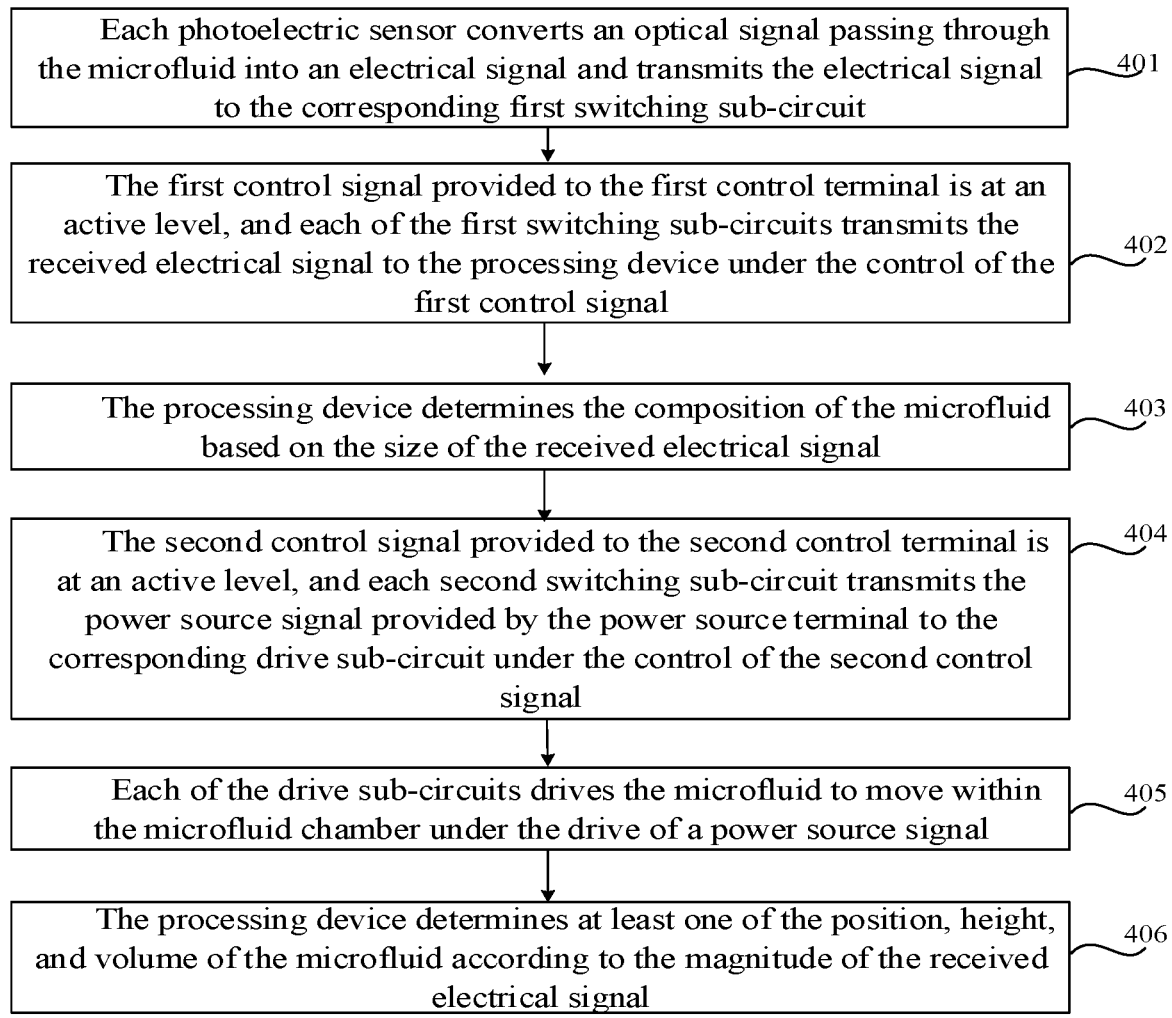
FIG. 10 is a flowchart of yet another microfluid detection method according to an embodiment of the present disclosure.

An embodiment of the present disclosure provides another microfluid detection method as shown in FIG. 10. This method is applied to the microfluid detection device as shown in FIG. 1 or FIG. 2. The method includes the following steps.

In step 401, each photoelectric sensor converts an optical signal passing through the microfluid into an electrical signal and transmits the electrical signal to the corresponding first switching sub-circuit.

Exemplarily, the photoelectric sensor may be a PIN photoelectric sensor. In the embodiment of the present disclosure, different light sources may be adopted to irradiate the microfluid, and light emitted by the light source passes through the microfluid a and irradiates the photoelectric sensor 140. Thus, the photoelectric sensor can convert the received optical signal into an electrical signal and transmits the electrical signal to the corresponding first switching sub-circuit. Here, the light source may be ambient light, infrared light or the like.

In step 402, the first control signal provided to the first control terminal is at an active level, and each of the first switching sub-circuits transmits the received electrical signal to the processing device under the control of the first control signal.

Optionally, as shown in FIG. 2, the first switching sub-circuit 150 may include a first switching transistor M0. Each of the first switching transistors M0 may be turned on when the first control signal provided by the first control terminal is at an active level, and receives the electrical signal transmitted by the photoelectric sensor 140 via the first electrode and transmits the received electrical signal to the processing device via the second electrode. Here, when the first switching transistor M0 is an N-type transistor, the active level may be a high level. When the first switching transistor M0 is a P-type transistor, the active level may be a low level.

In the embodiment of the present disclosure, for the plurality of first switching sub-circuits connected to the processing device by the same signal line, the first control terminals connected to the plurality of first switching sub-circuits may sequentially output the first control signals at the active level, such that the plurality of first switching sub-circuits can sequentially output the electrical signals to the processing device, thereby avoiding signal aliasing caused by output of electrical signals simultaneously by the plurality of first switching sub-circuits.

Exemplarily, as shown in FIG. 7, the first control terminals K1 may sequentially output the first control signals at an active level. The plurality of first switching sub-circuits 150 in the same column are turned on row by row and output the electrical signals to the processing device under the action of the received first control signals. The processing device 100 can determine the positions of the photoelectric sensors which generate the electrical signals based on the electrical signals received at different time, and can determine the composition of the microfluid a at the position based on the magnitude of the received electrical signals. Meanwhile, the processing device 100 may also determine at least one of the position, height, and volume of the microfluid a according to the positions of the plurality of photoelectric sensors and the magnitude of the received electrical signals.

In step 403, the processing device determines the composition of the microfluid based on the magnitude of the received electrical signal.

The processing device may determine the composition of the microfluid from a prestored first corresponding relationship according to the magnitude of the electrical signal, wherein the first corresponding relationship records a corresponding relationship between the magnitude of the electrical signal and the composition of the microfluid.

Exemplarily, the light source may adopt infrared light having a waveband from 770 nm (nanometer) to 1500 nm. During detection of the composition of the microfluid, the microfluid may be irradiated with infrared light of a certain wavelength within a preset time period. Since the amounts of infrared light of the same wavelength absorbed by the composition in the microfluid are different at different time points, the magnitude of the optical signals received by the photoelectric sensors at different time points is also different. The processing device can determine the composition of the microfluid from the prestored first corresponding relationship according to the magnitude of the electrical signals at different time points, and determine the composition of the microfluid according to the detection results at different time points. If the magnitude of the electrical signals received by the processing device at different points changes, it indicates that the content of the composition of the microfluid changes. For example, when the microfluid is irradiated with near-infrared light of a certain wavelength, the processing device determines that the composition of the microfluid is —OH (hydroxyl) according to the detection results at different time points, and the amount of the absorbed near-infrared light at different time points changes, and correspondingly, the magnitude of the electrical signal received by the processing device changes, then it reflects that the content of the —OH functional group in the microfluid changes.

It should be noted that when the composition of the microfluid is to be detected, it is necessary to adopt a corresponding light source according to the composition to be detected. If a chemical bond such as —OH, —NH (imino) or —CH (methine) in the microfluid needs to be detected, near-infrared light of an overtone region from 13158 cm-1 to 4000 cm-1 needs to be adopted. If the chemical bond vibration (i.e., the vibration of atoms in the molecule or the rotation of the molecule) of the organic compound and the inorganic compound in the microfluid needs to be detected, mid-infrared light having a basic vibration region from 4000 cm-1 to 400 cm-1 needs to be adopted. If the bond vibration (i.e., molecular rotation or lattice vibration) of the metal organic compound in the microfluid needs to be detected, far-infrared light having a molecular rotation region from 400 cm-1 to 10 cm-1 needs to be adopted. Here, cm-1 is a unit of wave number and is used to indicate the number of light waves per centimeter (cm).

In step 404, the second control signal provided to the second control terminal is at an active level, and each second switching sub-circuit transmits the power source signal provided by the power source terminal to the corresponding drive sub-circuit under the control of the second control signal.

Optionally, the microfluid detection device may further include: a plurality of drive sub-circuits 160 and a plurality of second switching sub-circuits 170 in a one-to-one correspondence with the plurality of drive sub-circuits 160. The second switching sub-circuit 170 may include a second switching transistor M1. Each of the second switching transistors M1 may be turned on when the second control signal provided by the second control terminal is at an active level, and receive a voltage signal transmitted by the power source terminal via the first electrode, and transmit the received voltage signal to the first electrode 001 via the second electrode. When the second switching transistor M1 is an N-type transistor, the active level may be a high level. When the second switching transistor M1 is a P-type transistor, the active level may be a low level. In the embodiment of the present disclosure, each of the drive sub-circuits 160 may include a first electrode 001 and a second electrode 002. The first electrode may be referred to as a drive electrode, and the second electrode may be referred to as a common electrode.

In step 405, each of the drive sub-circuits drives the microfluid to move within the microfluid chamber under the drive of a power source signal.

In the embodiment of the present disclosure, the second electrode 002 in each of the drive sub-circuits may be connected to the common power source terminal VSS or may be grounded. The first electrode 001 in each of the drive sub-circuits forms an electric field with the second electrode 002, under the drive of the power source signal. The electric field causes the wettability of the microfluid a on the surfaces of the first hydrophobic layer 005 and the second hydrophobic layer 006 to be changed from a hydrophobic state to a hydrophilic state, to drive the microfluid a to move within the microfluid chamber 130, to move to a designated position in the microfluid chamber 130.

Through step 404 and step 405, the drive circuit can be controlled to generate the electric field acting on the target hydrophobic layer. The target hydrophobic layer is configured to change in hydrophobicity under the action of the electric field, to drive the microfluid to move within the microfluid chamber.

In step 406, the processing device determines at least one of the position, height, and volume of the microfluid according to the magnitude of the received electrical signal.

Figure 11:
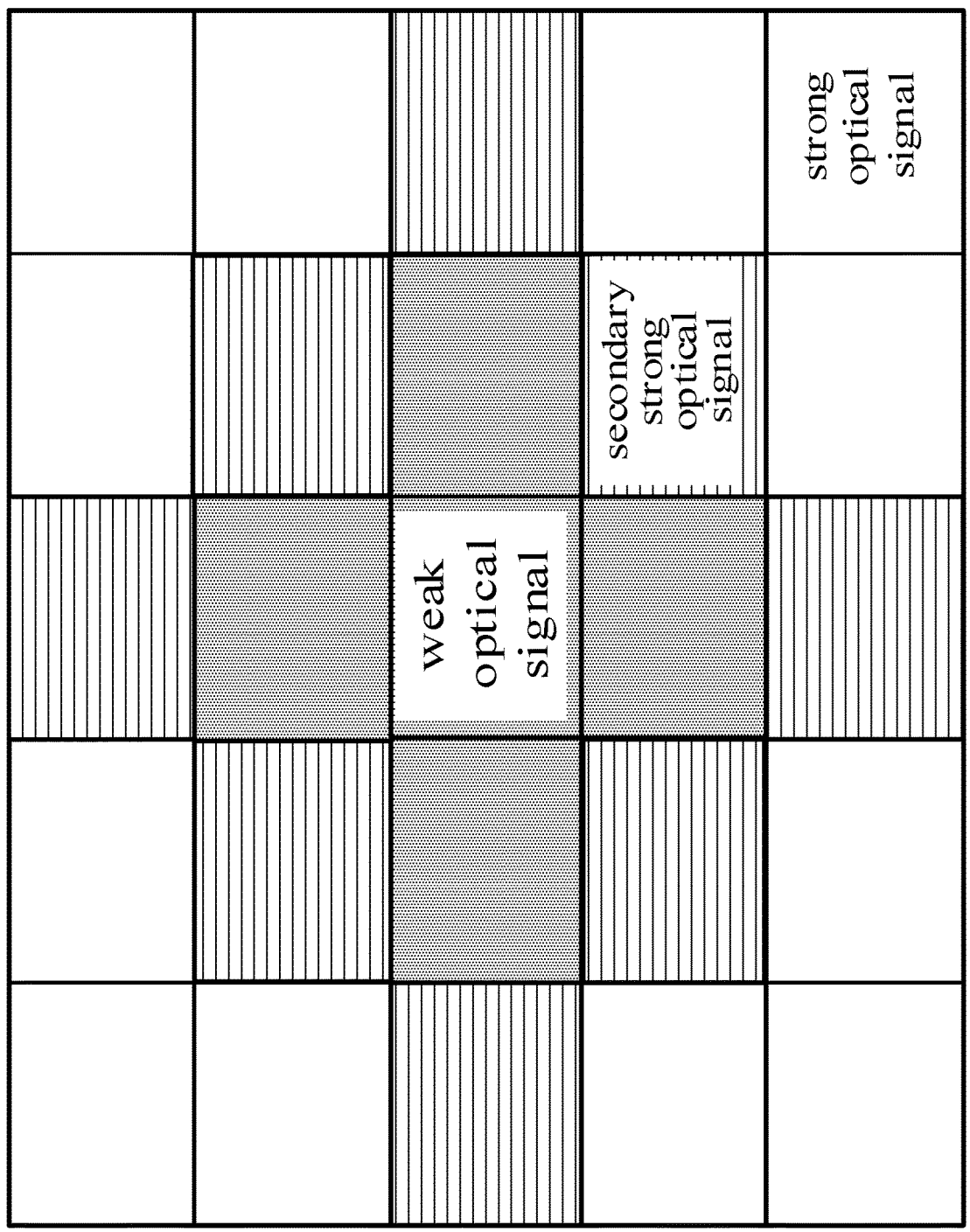

As shown in FIG. 5, light emitted by the light source passes through the microfluid a and irradiates the photoelectric sensor 140. Since blocking of the photoelectric sensors 140 by the microfluid a is different, intensity of the light received by the photoelectric sensors 140 is different. Therefore, the magnitude of the electrical signals generated according to the received optical signals is different. FIG. 11 shows a distribution diagram of the magnitude of the optical signals received by the photoelectric sensor. Referring to FIG. 11, the optical signal received by the photoelectric sensor which is blocked by the microfluid is a strong optical signal, the optical signal received by the photoelectric sensor which is partially blocked by the microfluid is a secondary strong optical signal, and the optical signal received by the photoelectric sensor which is completely blocked by the microfluid is a weak optical signal.

In the embodiment of the present disclosure, the position of the microfluid refers to the position that the photoelectric sensor receiving the weak optical signal and the secondary strong optical signal corresponds to. After determining the distribution of the magnitude of the optical signals, the processing device can determine the position of the microfluid according to the distribution of positions of the weak optical signal and the secondary strong optical signal.

In the embodiments of the present disclosure, the height of the microfluid refers to the height of the microfluid in a direction perpendicular to the first substrate, and the area of the microfluid refers to the area formed by the blocking of the photoelectric sensor by the microfluid. The processing device may determine the height of the microfluid from a prestored second corresponding relationship according to the magnitude of the electrical signal, and determine the volume of the microfluid according to the height of the microfluid and the area of the microfluid. The corresponding relationship between the magnitude of the electrical signal and the height of the microfluid is recorded in the second corresponding relationship.

In the embodiment of the present disclosure, detection of the position of the microfluid and the volume of the microfluid may be performed by an ambient light source or an ordinary light source. Here, the ordinary light source refers to a light source which emits light of a single wavelength. The detection of the position of the microfluid, the volume of the microfluid, and the composition of the microfluid may be performed simultaneously or separately, which is not limited in the embodiment of the present disclosure.

It should be noted that the sequence of the steps in the microfluid detection method provided in the embodiment of the present disclosure may be appropriately adjusted, and the steps may also be correspondingly added or deleted based on situation. Any variable method which is readily conceivable to those skilled in the art within the scope of the present disclosure shall be included in the protection scope of the present disclosure, and therefore will not be described again.

In summary, according to the microfluid detection method provided by the embodiment of the present disclosure, each photoelectric sensor converts an optical signal passing through the microfluid into an electrical signal, and transmits the electrical signal to the corresponding first switching sub-circuit. Each first switching sub-circuit transmits the received electrical signal to the processing device under the control of the first control signal provided by the first control terminal, and the processing device determines the composition of the microfluid according to the magnitude of the received electrical signal. Compared with the related art, the photoelectric sensors are more sensitive in detection of the change in the composition of the microfluid, and the accuracy of detection of the composition of microfluid is improved.

Figure 12:
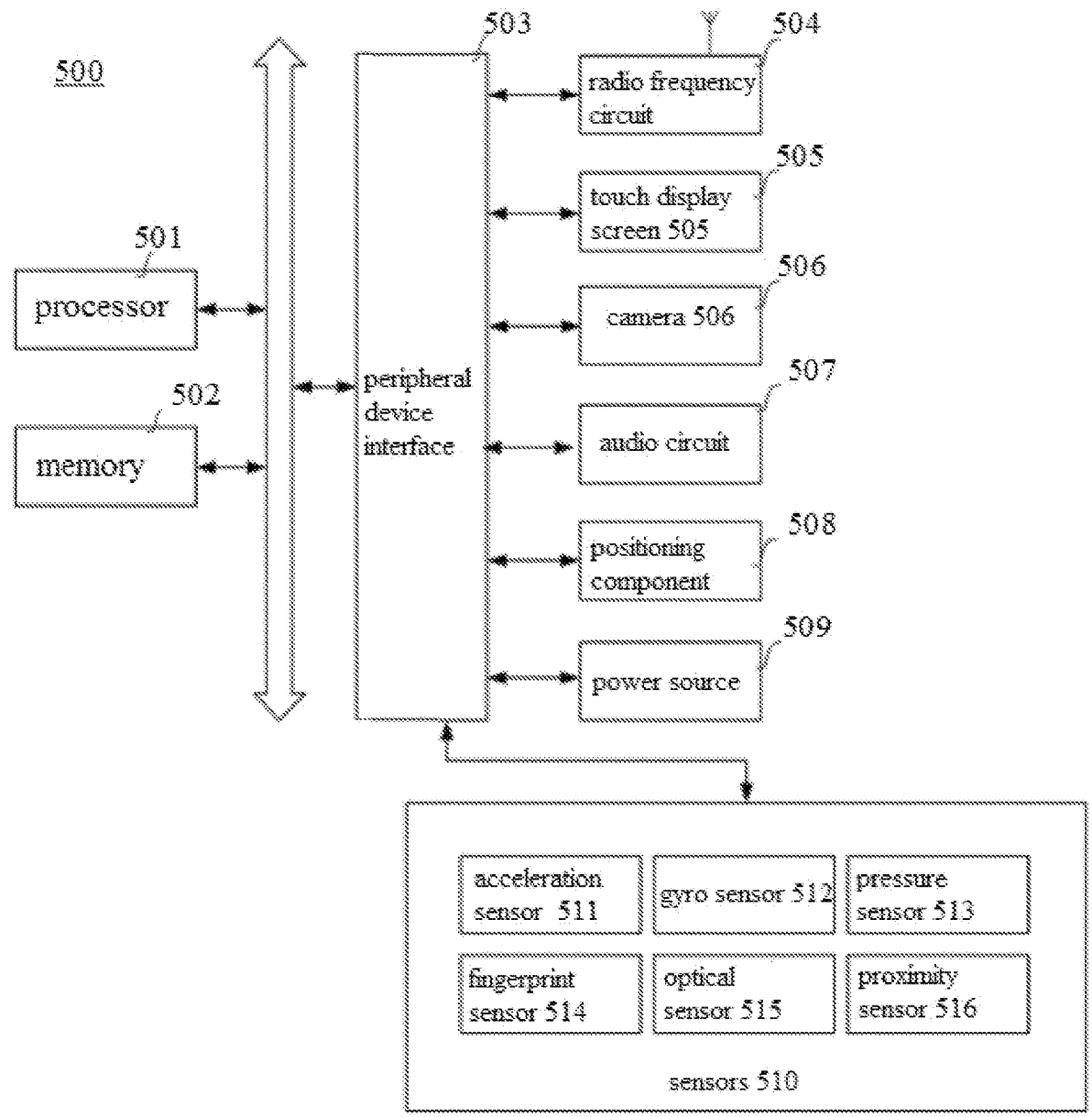
FIG. 12 is a structural block diagram of a processing device according to an embodiment of the present disclosure.

FIG. 12 is a structural block diagram of a processing device 500 according to the embodiment of the present disclosure. Generally, the device 500 includes a processor 501 and a memory 502.

The processor 501 may include one or more processing cores, such as a 4-core processor, an 8-core processor, etc. The processor 501 may be implemented by at least one hardware of a Digital Signal Processing (DSP), a Field-Programmable Gate Array (FPGA), and a Programmable Logic Array (PLA). The processor 501 may also include a host processor and a coprocessor. The host processor is a processor configured to process data in a wake state, and is also called a Central Processing Unit (CPU). The coprocessor is a low-power consumption processor configured to process data in a standby state. In some embodiments, the processor 501 may be integrated with a Graphics Processing Unit (GPU), which configured to be responsible for rendering and drawing of the content to be displayed by a display screen. In some embodiments, the processor 501 may also include an Artificial Intelligence (AI) processor configured to process the computational operations related to machine learning.

The memory 502 may include one or more computer readable storage mediums, which may be non-transitory. The memory 502 may also include a high speed random access memory, as well as non-volatile memories, such as one or more disk storage devices and flash storage devices. In some embodiments, the non-transitory computer readable storage medium in the memory 502 is configured to store at least one instruction. The at least one instruction is executed by the processor 501 to implement the methods provided in the method embodiments of the present disclosure.

In some embodiments, optionally, the device 500 also includes a peripheral device interface 503 and at least one peripheral device. The processor 501, the memory 502, and the peripheral device interface 503 may be connected by a bus or a signal line. The peripheral devices may be connected to the peripheral device interface 503 by buses, signal lines or circuit boards. Specifically, the peripheral devices include at least one of a radio frequency circuit 504, a touch display screen 505, a camera 506, an audio circuit 507, a positioning component 508, and a power source 509.

The peripheral device interface 503 may be configured to connect at least one peripheral device associated with an Input/Output (I/O) to the processor 501 and the memory 502. In some embodiments, the processor 501, the memory 502, and the peripheral device interface 503 are integrated on the same chip or circuit board. In some other embodiments, any one or two of the processor 501, the memory 502, and the peripheral device interface 503 may be implemented on a separate chip or circuit board, which is not limited in the present embodiment.

The radio frequency circuit 504 is configured to receive and transmit Radio Frequency (RF) signal, which is also referred to as electromagnetic signals. The radio frequency circuit 504 communicates with a communication network and other communication devices via the electromagnetic signals. The radio frequency circuit 504 converts electrical signals into electromagnetic signals for transmission, or converts the received electromagnetic signals into electrical signals. Optionally, the radio frequency circuit 504 includes: an antenna system, an RF transceiver, one or more amplifiers, a tuner, an oscillator, a digital signal processor, a codec chipset, a subscriber identity module card, and the like. The radio frequency circuit 504 can communicate with other terminals via at least one wireless communication protocol. The wireless communication protocol includes, but is not limited to, a metropolitan area network, varied generations of mobile communication networks (2G, 3G, 4G, and 5G), a wireless local area network, and/or a Wireless Fidelity (WiFi) network. In some embodiments, the radio frequency circuit 504 may further include Close to Field Communication (NFC) related circuits, which is not limited in the present disclosure.

The display screen 505 is configured to display a User Interface (UI). The UI may include graphics, text, icons, videos, and any combination thereof. When the display screen 505 is a touch display screen, the display screen 505 also has the capacity for acquiring touch signals on or over the surface of the display screen 505. The touch signals may be input to the processor 501 as control signals for processing. In this case, the display screen 505 may also be configured to provide virtual buttons and/or virtual keyboards, which are also referred to as soft buttons and/or soft keyboards. In some embodiments, there may be one display screen 505 which is disposed on the front panel of the device 500. In some other embodiments, there may be at least two display screens 505, which are respectively disposed on different surfaces of the device 500 or in a folded design. In still other embodiments, the display screen 505 may be a flexible display screen disposed on a curved surface or folded surface of the device 500. Even, the display screen 505 may be set to a non-rectangular irregular pattern, that is, a profiled screen. The display screen 505 may be manufactured with materials, such as a Liquid Crystal Display (LCD) or an Organic Light-Emitting Diode (OLED).

The camera component 506 is configured to capture images or videos. Optionally, the camera component 506 includes a front camera and a rear camera. Usually, the front camera is disposed on the front panel of the terminal, and the rear camera is disposed on the back of the terminal. In some embodiments, there are at least two rear cameras, each of which is any of a main camera, a depth camera, a wide-angle camera, and a telephoto camera respectively, to realize the background blur function achieved by the fusion of the main camera and the depth camera, the panoramic shooting and Virtual Reality (VR) shooting functions achieved by the fusion of the main camera and the wide-angle camera or other fusion shooting functions. In some embodiments, the camera component 506 may also include a flashlight. The flashlight may be a mono-color temperature flashlight or a double color temperature flashlight. The double color temperature flashlight is the combination of a warm flashlight and a cool flashlight and can be used for light compensation at different color temperatures.

The audio circuit 507 may include a microphone and a loudspeaker. The microphone is configured to collect sound waves from users and the environment, and convert the sound waves into electrical signals and then input the electrical signals to the processor 501 for processing, or input the electrical signals to the radio frequency circuit 504 to achieve voice communication. For the purpose of stereo acquisition or noise reduction, there may be a plurality of microphones, which are respectively disposed at different positions of the device 500. The microphone may also be an array microphone or an omnidirectional acquisition microphone. The loudspeaker is configured to convert the electrical signals from the processor 501 or radio frequency circuit 504 into sound waves. The loudspeaker may be a conventional film loudspeaker or a piezoelectric ceramic loudspeaker. When the loudspeaker is a piezoelectric ceramic loudspeaker, it can not only convert electrical signals into human-audible sound waves, but also convert the electrical signals into sound waves which are inaudible to humans for the purposes of distance measurement and the like. In some embodiments, the audio circuit 507 may further include a headset jack.

The positioning component 508 is configured to locate the current geographic location of the device 500, to implement navigation or Location Based Service (LBS). The positioning component 508 may be a positioning component based on American Global Positioning System (GPS), Chinese Beidou system, Russian Greiner system, or EU Galileo system.

The power source 509 is configured to power varied components in the device 500. The power source 509 may be alternating current, direct current, a disposable battery, or a rechargeable battery. When the power source 509 includes a rechargeable battery, the rechargeable battery can support wired charging or wireless charging. The rechargeable battery may also support the fast charging technology.

In some embodiments, device 500 further includes one or more sensors 510. The one or more sensors 510 include, but are not limited to, an acceleration sensor 511, a gyro sensor 512, a pressure sensor 513, a fingerprint sensor 514, an optical sensor 515, and a proximity sensor 516.

It will be understood by those skilled in the art that the structure shown in FIG. 12 does not limit on the device 500, and the device 500 may include more or less components than those illustrated, or combination of some components or adopt different arrangements of components.

In exemplary embodiments, there is further provided a non-transitory computer readable storage medium including instructions, such as a memory including instructions. The instructions may be executed by the processor of a server to implement the methods in varied embodiments of the present disclosure. For example, the non-transitory computer readable storage medium may be an ROM, a random access memory (RAM), a CD-ROM, a magnetic tape, a floppy disk, an optical data storage device, etc.

The foregoing descriptions are merely exemplary embodiments of the present disclosure, and are not intended to limit the present disclosure. Within the spirit and principles of the disclosure, any modifications, equivalent substitutions, improvements, etc., are within the protection scope of the appended claims of the present disclosure.

What is claimed is:

1. A microfluid detection device, comprising:
 a first substrate and a second substrate facing each other, and a microfluid chamber between the first substrate and the second substrate; wherein
 the first substrate has a plurality of photoelectric sensors and an output circuit connected to the plurality of photoelectric sensors, each of the photoelectric sensors is configured to convert an optical signal passing through the second substrate and the microfluid chamber to an electrical signal, and the output circuit is configured to output the electrical signal obtained by the photoelectric sensor,
 wherein the electrical signal is configured to determine composition, a position, height, and a volume of microfluid; the optical signal is generated after light emitted by an infrared light source passes through the microfluid; and amounts of infrared light of the same wavelength absorbed by the composition in the microfluid are different at different time points.

2. The microfluid detection device according to claim 1, wherein the output circuit comprises:
   a plurality of first switching sub-circuits in a one-to-one correspondence with the plurality of photoelectric sensors, wherein each of the first switching sub-circuits has an input terminal, an output terminal, and a first control terminal, and the input terminal of the first switching sub-circuit is connected to the corresponding photoelectric sensor; and
   each of the first switching sub-circuits is configured to output the electrical signal obtained by the corresponding photoelectric sensor from the output terminal of the first switching sub-circuit under the control of a control signal provided by the first control terminal.

3. The microfluid detection device according to claim 2, wherein the first switching sub-circuit comprises: a first switching transistor, wherein a gate electrode of the first switching transistor is connected to the first control terminal, a first electrode of the first switching transistor is connected to the input terminal of the first switching sub-circuit, and a second electrode of the first switching transistor is connected to the output terminal of the first switching sub-circuit.

4. The microfluid detection device according to claim 2, wherein the plurality of first switching sub-circuits is disposed in an array on the first substrate;
   first control terminals of the plurality of first switching sub-circuits disposed along a first direction are connected to a same control line, and output terminals of the plurality of first switching sub-circuits disposed along a second direction are connected to a same signal line;
   wherein the first direction is one of a row direction and a column direction, and the second direction is the other one of the row direction and the column direction.

5. The microfluid detection device according to claim 1, further comprising:
   at least one of a first hydrophobic layer and a second hydrophobic layer, wherein the first hydrophobic layer is on a side surface, close to the microfluid chamber, of the first substrate and the second hydrophobic layer is on a side surface, close to the microfluid chamber, of the second substrate.

6. The microfluid detection device according to claim 5, further comprising:
   a drive circuit, configured to provide an electric field acting on a target hydrophobic layer; wherein
   the target hydrophobic layer is configured to change in hydrophobicity under the action of the electric field, to drive microfluid to move within the microfluid chamber; and
   the target hydrophobic layer comprises at least one of the first hydrophobic layer and the second hydrophobic layer.

7. The microfluid detection device according to claim 6, wherein the drive circuit comprises:
   a power source terminal, configured to provide a power source signal;
   a plurality of drive sub-circuits, configured to provide an electric field to different regions of the target hydrophobic layer; and
   a plurality of second switching sub-circuits, wherein the plurality of second switching sub-circuits are in a one-to-one correspondence with the plurality of drive sub-circuits, the second switching sub-circuit has an input terminal, an output terminal, and a second control terminal, the input terminal of the second switching sub-circuit is connected to the power source terminal, the output terminal of the second switching sub-circuit is connected to the corresponding drive sub-circuit, and the second switching sub-circuit is configured to transmit the power source signal provided by the power source terminal to the corresponding drive sub-circuit under the control of a control signal provided by the second control terminal, to enable the corresponding drive sub-circuit to provide an electric field to the target hydrophobic layer.

8. The microfluid detection device according to claim 7, wherein each of the drive sub-circuits comprises a first electrode and a second electrode, each of the second switching sub-circuits is connected to the first electrode in the corresponding drive sub-circuit respectively, and the second switching sub-circuit is on the same substrate as the first electrode; and
   the first electrode and the second electrode in each of the drive sub-circuits are disposed in any one of the following manners:
   the first electrode and the second electrode are spaced apart from each other in an insulating manner at a side, close to the microfluid chamber, of the first substrate;
   the first electrode and the second electrode are spaced apart from each other in an insulating manner at a side, close to the microfluid chamber, of the second substrate;
   the first electrode is at a side, close to the microfluid chamber, of the first substrate, and the second electrode is at a side, close to the microfluid chamber, of the second substrate; and
   the first electrode is at a side, close to the microfluid chamber, of the second substrate, and the second electrode is at a side, close to the microfluid chamber, of the first substrate.

9. The microfluid detection device according to claim 7, wherein the second electrodes in the plurality of drive sub-circuits are of an integral structure; and
   an orthographic projection of the first electrode on the substrate which the second electrode is on and the integral structure meet any one of the following relationships:
   the integral structure is grid-shaped, and the orthographic projection of the first electrode on the substrate which the second electrode is on is within a grid of the grid-shaped integral structure; and
   the integral structure is block-shaped, and the orthographic projection of the first electrode on the substrate which the second electrode is on is within the block-shaped integral structure.

10. The microfluid detection device according to claim 7, wherein the first electrodes and the second electrodes in the plurality of drive sub-circuits are in an array; and
    the substrate which the second electrodes are on has a plurality of regions in an array, and each of the regions has one of the first electrodes and one of the second electrodes which are spaced apart.

11. The microfluid detection device according to claim 7, wherein each of the second switching sub-circuits comprises: a second switching transistor;
    wherein a gate electrode of the second switching transistor is connected to the second control terminal, a first electrode of the second switching transistor is connected to the input terminal of the second switching sub-circuit, and a second electrode of the second switching transistor is connected to the output terminal of the second switching sub-circuit.

12. The microfluid detection device according to claim 6, wherein the target hydrophobic layer is made of polytetrafluoroethylene.

13. A microfluid detection system, comprising: a microfluid detection device and a processing device, wherein
the microfluid detection device comprises: a first substrate and a second substrate facing each other, and a microfluid chamber between the first substrate and the second substrate;
the first substrate has a plurality of photoelectric sensors and an output circuit connected to the plurality of photoelectric sensors, each of the photoelectric sensors is configured to convert an optical signal passing through the second substrate and the microfluid chamber to an electrical signal, and the output circuit is configured to output the electrical signal obtained by the photoelectric sensor; and
the processing device is connected to the output circuit, and the processing device is configured to receive the electrical signal output by the output circuit and to determine composition, a position, height, and a volume of microfluid based on the received electrical signal,
wherein the optical signal is generated after light emitted by an infrared light source passes through the microfluid, and amounts of infrared light of the same wavelength absorbed by the composition in the microfluid are different at different time points.

14. A microfluid detection method, applied to a microfluid detection device, wherein the microfluid detection device comprises a first substrate and a second substrate facing each other, and a microfluid chamber between the first substrate and the second substrate; the first substrate has a plurality of photoelectric sensors and an output circuit connected to the plurality of photoelectric sensors, each of the photoelectric sensors is configured to convert an optical signal passing through the second substrate and the microfluid chamber to an electrical signal, and the output circuit is configured to output the electrical signal obtained by the photoelectric sensor, and the method comprises:
receiving the electrical signal output by the output circuit; and
determining composition, a position, height, and a volume of microfluid based on the received electrical signal,
wherein the optical signal is generated after light emitted by an infrared light source passes through the microfluid, and amounts of infrared light of the same wavelength absorbed by the composition in the microfluid are different at different time points.

15. The microfluid detection method according to claim 14, wherein determining the composition of microfluid based on the received electrical signal comprises:
determining, according to magnitude of the electrical signal, the composition of the microfluid from a pre-stored first corresponding relationship, wherein the first corresponding relationship is configured to record a corresponding relationship between the magnitude of the electrical signal and the composition of the microfluid, and the magnitude of the electrical signal is voltage magnitude of the electrical signal or the current magnitude of the electrical signal.

16. The microfluid detection method according to claim 14, wherein the output circuit comprises:
a plurality of first switching sub-circuits in a one-to-one correspondence with the plurality of photoelectric sensors, wherein each of the first switching sub-circuits has an input terminal, an output terminal, and a first control terminal, and the input terminal of the first switching sub-circuit is connected to the corresponding photoelectric sensor; and
the method further comprises: providing a control signal to the first control terminal, to enable the first switching sub-circuit to output the electrical signal obtained by the corresponding photoelectric sensor from the output terminal of the first switching sub-circuit under the control of the control signal provided by the first control terminal.

17. The microfluid detection method according to claim 14, wherein the microfluid detection device further comprises at least one of a first hydrophobic layer and a second hydrophobic layer, and a drive circuit, wherein the first hydrophobic layer is on a side surface, close to the microfluid chamber, of the first substrate and the second hydrophobic layer is on a side surface, close to the microfluid chamber, of the second substrate; the method further comprises:
controlling the drive circuit to generate an electric field acting on a target hydrophobic layer, wherein the target hydrophobic layer is configured to change in hydrophobicity under the action of the electric field, to drive the microfluid to move within the microfluid chamber;
wherein the target hydrophobic layer comprises at least one of the first hydrophobic layer and the second hydrophobic layer.

18. A processing device, comprising: a processor; and a memory configured to store instructions executable by the processor; wherein the processor is configured to implement the method according to claim 14.

19. A computer readable storage medium, capable of implementing the method according to claim 14 when instructions in the computer readable storage medium are executed by a processor.

* * * * *